(12) United States Patent
Fitzsimmons et al.

(10) Patent No.: US 10,842,758 B1
(45) Date of Patent: Nov. 24, 2020

(54) TRANSDERMAL PENETRANT FORMULATIONS CONTAINING CANNABIDIOL

(71) Applicant: AMPERSAND BIOPHARMACEUTICALS, INC., Thousand Oaks, CA (US)

(72) Inventors: Nathan Fitzsimmons, Thousand Oaks, CA (US); Ryan Beal, Thousand Oaks, CA (US); Audrene McMahon, Thousand Oaks, CA (US); Brandon Sand, Thousand Oaks, CA (US); Kilmar Martinez, Thousand Oaks, CA (US)

(73) Assignee: AMPERSAND BIOPHARMACEUTICALS, INC., Thousand Oaks, CA (US)

( * ) Notice: Subject to any disclaimer, the term of this patent is extended or adjusted under 35 U.S.C. 154(b) by 0 days.

(21) Appl. No.: 16/546,269

(22) Filed: Aug. 20, 2019

Related U.S. Application Data

(60) Provisional application No. 62/863,236, filed on Jun. 18, 2019.

(51) Int. Cl.
| | | |
|---|---|---|
| *A61K 31/05* | (2006.01) | |
| *A61K 9/06* | (2006.01) | |
| *A61K 47/24* | (2006.01) | |
| *A61K 47/26* | (2006.01) | |
| *A61K 9/00* | (2006.01) | |
| *A61K 47/44* | (2017.01) | |
| *A61K 47/12* | (2006.01) | |
| *A61K 47/14* | (2017.01) | |
| *A61K 47/10* | (2017.01) | |

(52) U.S. Cl.
CPC ............ *A61K 31/05* (2013.01); *A61K 9/0014* (2013.01); *A61K 9/06* (2013.01); *A61K 47/10* (2013.01); *A61K 47/12* (2013.01); *A61K 47/14* (2013.01); *A61K 47/24* (2013.01); *A61K 47/26* (2013.01); *A61K 47/44* (2013.01)

(58) Field of Classification Search
CPC ........ A61K 47/10; A61K 47/12; A61K 47/14; A61K 47/24; A61K 47/26; A61K 47/44; A61K 31/05
See application file for complete search history.

(56) References Cited

U.S. PATENT DOCUMENTS

2016/0303039 A1* 10/2016 Smith .................. A61K 31/352

OTHER PUBLICATIONS

Raut et al. Acta Pharmaceutica Sinica B, 2012, vol. 2, No. 1, pp. 8-15 (Year: 2012).*
Scholfield (Journal of the American Oil Chemists' Society, Oct. 1981, vol. 58, No. 10, pp. 889-892) (Year: 1981).*

* cited by examiner

*Primary Examiner* — James D. Anderson
(74) *Attorney, Agent, or Firm* — Entralta P.C.; Peter D. Weinstein; James F. Fleming

(57) ABSTRACT

Disclosed herein is a transdermal delivery formulation for transdermal delivery of a Cannabidiol, with or without one or more additional active agents through the dermis, including the skin, nail or hair follicle of a subject, wherein the formulation comprises a) a transdermal delivery formulation in an amount less than about 60% w/w, comprising i. one or more phosphatides, ii. glucose, and iii. one or more fatty acids; b) water in an amount less than about 50% w/w, a Cannabidiol with or within one or more additional active agents.

16 Claims, 27 Drawing Sheets

Abemaciclib

Abiraterone Acetate

Abraxane (Paclitaxel Albumin-stabilized Nanoparticle Formulation)

ABVD

ABVE

ABVE-PC

AC

Acalabrutinib

AC-T

Actemra (Tocilizumab)

Adcetris (Brentuximab Vedotin)

ADE

Ado-Trastuzumab Emtansine

Adriamycin (Doxorubicin Hydrochloride)

Afatinib Dimaleate

Afinitor (Everolimus)

Akynzeo (Netupitant and Palonosetron Hydrochloride)

Aldara (Imiquimod)

Aldesleukin

Alecensa (Alectinib)

Alectinib

Alemtuzumab

Alimta (Pemetrexed Disodium)

Aliqopa (Copanlisib Hydrochloride)

Alkeran for Injection (Melphalan Hydrochloride)

Alkeran Tablets (Melphalan)

Aloxi (Palonosetron Hydrochloride)

Alunbrig (Brigatinib)

Ameluz (Aminolevulinic Acid Hydrochloride)

Amifostine

FIG. 9B

Aminolevulinic Acid Hydrochloride

Anastrozole

Apalutamide

Aprepitant

Aranesp (Darbepoetin Alfa)

Aredia (Pamidronate Disodium)

Arimidex (Anastrozole)

Aromasin (Exemestane)

Arranon (Nelarabine)

Arsenic Trioxide

Arzerra (Ofatumumab)

Asparaginase Erwinia chrysanthemi

Asparlas (Calaspargase Pegol-mknl)

Atezolizumab

Avastin (Bevacizumab)

Avelumab

Axicabtagene Ciloleucel

Axitinib

Azacitidine

Azedra (Iobenguane I 131)

B

Balversa (Erdafitinib)

Bavencio (Avelumab)

BEACOPP

Beleodaq (Belinostat)

Belinostat

Bendamustine Hydrochloride

Bendeka (Bendamustine Hydrochloride)

BEP

Besponsa (Inotuzumab Ozogamicin)

Bevacizumab

FIG. 9C

Bexarotene
Bicalutamide
BiCNU (Carmustine)
Binimetinib
Bleomycin Sulfate
Blinatumomab
Blincyto (Blinatumomab)
Bortezomib
Bosulif (Bosutinib)
Bosutinib
Braftovi (Encorafenib)
Brentuximab Vedotin
Brigatinib
BuMel
Busulfan
Busulfex (Busulfan)
C
Cabazitaxel
Cablivi (Caplacizumab-yhdp)
Cabometyx (Cabozantinib-S-Malate)
Cabozantinib-S-Malate
CAF
Calaspargase Pegol-mknl
Calquence (Acalabrutinib)
Campath (Alemtuzumab)
Camptosar (Irinotecan Hydrochloride)
Capecitabine
Caplacizumab-yhdp
CAPOX
Carac (Fluorouracil--Topical)
Carboplatin

FIG. 9D

CARBOPLATIN-TAXOL
Carfilzomib
Carmustine
Carmustine Implant
Casodex (Bicalutamide)
CEM
Cemiplimab-rwlc
Ceritinib
Cerubidine (Daunorubicin Hydrochloride)
Cervarix (Recombinant HPV Bivalent Vaccine)
Cetuximab
CEV
Chlorambucil
CHLORAMBUCIL-PREDNISONE
CHOP
Cisplatin
Cladribine
Clofarabine
Clolar (Clofarabine)
CMF
Cobimetinib
Cometriq (Cabozantinib-S-Malate)
Copanlisib Hydrochloride
COPDAC
Copiktra (Duvelisib)
COPP
COPP-ABV
Cosmegen (Dactinomycin)
Cotellic (Cobimetinib)
Crizotinib
CVP

FIG. 9E

Cyclophosphamide
Cyramza (Ramucirumab)
Cytarabine
Cytarabine Liposome
Cytosar-U (Cytarabine)
D
Dabrafenib
Dacarbazine
Dacogen (Decitabine)
Dacomitinib
Dactinomycin
Daratumumab
Darbepoetin Alfa
Darzalex (Daratumumab)
Dasatinib
Daunorubicin Hydrochloride
Daunorubicin Hydrochloride and Cytarabine Liposome
Daurismo (Glasdegib Maleate)
Decitabine
Defibrotide Sodium
Defitelio (Defibrotide Sodium)
Degarelix
Denileukin Diftitox
Denosumab
DepoCyt (Cytarabine Liposome)
Dexamethasone
Dexrazoxane Hydrochloride
Dinutuximab
Docetaxel
Doxil (Doxorubicin Hydrochloride Liposome)
Doxorubicin Hydrochloride

FIG. 9F

Doxorubicin Hydrochloride Liposome
Dox-SL (Doxorubicin Hydrochloride Liposome)
Durvalumab
Duvelisib
E
Efudex (Fluorouracil--Topical)
Eligard (Leuprolide Acetate)
Elitek (Rasburicase)
Ellence (Epirubicin Hydrochloride)
Elotuzumab
Eloxatin (Oxaliplatin)
Eltrombopag Olamine
Elzonris (Tagraxofusp-erzs)
Emapalumab-lzsg
Emend (Aprepitant)
Empliciti (Elotuzumab)
Enasidenib Mesylate
Encorafenib
Enzalutamide
Epirubicin Hydrochloride
EPOCH
Epoetin Alfa
Epogen (Epoetin Alfa)
Erbitux (Cetuximab)
Erdafitinib
Eribulin Mesylate
Erivedge (Vismodegib)
Erleada (Apalutamide)
Erlotinib Hydrochloride
Erwinaze (Asparaginase Erwinia chrysanthemi)
Ethyol (Amifostine)

FIG. 9G

Etopophos (Etoposide Phosphate)
Etoposide
Etoposide Phosphate
Evacet (Doxorubicin Hydrochloride Liposome)
Everolimus
Evista (Raloxifene Hydrochloride)
Evomela (Melphalan Hydrochloride)
Exemestane
F
5-FU (Fluorouracil Injection)
5-FU (Fluorouracil--Topical)
Fareston (Toremifene)
Farydak (Panobinostat)
Faslodex (Fulvestrant)
FEC
Femara (Letrozole)
Filgrastim
Firmagon (Degarelix)
Fludarabine Phosphate
Fluoroplex (Fluorouracil--Topical)
Fluorouracil Injection
Fluorouracil--Topical
Flutamide
FOLFIRI
FOLFIRI-BEVACIZUMAB
FOLFIRI-CETUXIMAB
FOLFIRINOX
FOLFOX
Folotyn (Pralatrexate)
Fostamatinib Disodium
FU-LV

FIG. 9H

Fulvestrant

Fusilev (Leucovorin Calcium)

G

Gamifant (Emapalumab-lzsg)

Gardasil (Recombinant HPV Quadrivalent Vaccine)

Gardasil 9 (Recombinant HPV Nonavalent Vaccine)

Gazyva (Obinutuzumab)

Gefitinib

Gemcitabine Hydrochloride

GEMCITABINE-CISPLATIN

GEMCITABINE-OXALIPLATIN

Gemtuzumab Ozogamicin

Gemzar (Gemcitabine Hydrochloride)

Gilotrif (Afatinib Dimaleate)

Gilteritinib Fumarate

Glasdegib Maleate

Gleevec (Imatinib Mesylate)

Gliadel Wafer (Carmustine Implant)

Glucarpidase

Goserelin Acetate

Granisetron

Granisetron Hydrochloride

Granix (Filgrastim)

H

Halaven (Eribulin Mesylate)

Hemangeol (Propranolol Hydrochloride)

Herceptin Hylecta (Trastuzumab and Hyaluronidase-oysk)

Herceptin (Trastuzumab)

HPV Bivalent Vaccine, Recombinant

HPV Nonavalent Vaccine, Recombinant

HPV Quadrivalent Vaccine, Recombinant

FIG. 9I

Hycamtin (Topotecan Hydrochloride)
Hydrea (Hydroxyurea)
Hydroxyurea
Hyper-CVAD
I
Ibrance (Palbociclib)
Ibritumomab Tiuxetan
Ibrutinib
ICE
Iclusig (Ponatinib Hydrochloride)
Idarubicin Hydrochloride
Idelalisib
Idhifa (Enasidenib Mesylate)
Ifex (Ifosfamide)
Ifosfamide
IL-2 (Aldesleukin)
Imatinib Mesylate
Imbruvica (Ibrutinib)
Imfinzi (Durvalumab)
Imiquimod
Imlygic (Talimogene Laherparepvec)
Inlyta (Axitinib)
Inotuzumab Ozogamicin
Interferon Alfa-2b, Recombinant
Interleukin-2 (Aldesleukin)
Intron A (Recombinant Interferon Alfa-2b)
Iobenguane I 131
Ipilimumab
Iressa (Gefitinib)
Irinotecan Hydrochloride
Irinotecan Hydrochloride Liposome

FIG. 9J

Istodax (Romidepsin)
Ivosidenib
Ixabepilone
Ixazomib Citrate
Ixempra (Ixabepilone)
J
Jakafi (Ruxolitinib Phosphate)
JEB
Jevtana (Cabazitaxel)
K
Kadcyla (Ado-Trastuzumab Emtansine)
Kepivance (Palifermin)
Keytruda (Pembrolizumab)
Kisqali (Ribociclib)
Kymriah (Tisagenlecleucel)
Kyprolis (Carfilzomib)
L
Lanreotide Acetate
Lapatinib Ditosylate
Larotrectinib Sulfate
Lartruvo (Olaratumab)
Lenalidomide
Lenvatinib Mesylate
Lenvima (Lenvatinib Mesylate)
Letrozole
Leucovorin Calcium
Leukeran (Chlorambucil)
Leuprolide Acetate
Levulan Kerastik (Aminolevulinic Acid Hydrochloride)
Libtayo (Cemiplimab-rwlc)
LipoDox (Doxorubicin Hydrochloride Liposome)

FIG. 9K

Lomustine

Lonsurf (Trifluridine and Tipiracil Hydrochloride)

Lorbrena (Lorlatinib)

Lorlatinib

Lumoxiti (Moxetumomab Pasudotox-tdfk)

Lupron (Leuprolide Acetate)

Lupron Depot (Leuprolide Acetate)

Lutathera (Lutetium Lu 177-Dotatate)

Lutetium (Lu 177-Dotatate)

Lynparza (Olaparib)

M

Marqibo (Vincristine Sulfate Liposome)

Matulane (Procarbazine Hydrochloride)

Mechlorethamine Hydrochloride

Megestrol Acetate

Mekinist (Trametinib)

Mektovi (Binimetinib)

Melphalan

Melphalan Hydrochloride

Mercaptopurine

Mesna

Mesnex (Mesna)

Methotrexate

Methylnaltrexone Bromide

Midostaurin

Mitomycin C

Mitoxantrone Hydrochloride

Mogamulizumab-kpkc

Moxetumomab Pasudotox-tdfk

Mozobil (Plerixafor)

Mustargen (Mechlorethamine Hydrochloride)

FIG. 9L

MVAC
Mvasi (Bevacizumab)
Myleran (Busulfan)
Mylotarg (Gemtuzumab Ozogamicin)
N
Nanoparticle Paclitaxel (Paclitaxel Albumin-stabilized Nanoparticle Formulation)
Navelbine (Vinorelbine Tartrate)
Necitumumab
Nelarabine
Neratinib Maleate
Nerlynx (Neratinib Maleate)
Netupitant and Palonosetron Hydrochloride
Neulasta (Pegfilgrastim)
Neupogen (Filgrastim)
Nexavar (Sorafenib Tosylate)
Nilandron (Nilutamide)
Nilotinib
Nilutamide
Ninlaro (Ixazomib Citrate)
Niraparib Tosylate Monohydrate
Nivolumab
Nplate (Romiplostim)
O
Obinutuzumab
Odomzo (Sonidegib)
OEPA
Ofatumumab
OFF
Olaparib
Olaratumab
Omacetaxine Mepesuccinate

FIG. 9M

Oncaspar (Pegaspargase)

Ondansetron Hydrochloride

Onivyde (Irinotecan Hydrochloride Liposome)

Ontak (Denileukin Diftitox)

Opdivo (Nivolumab)

OPPA

Osimertinib Mesylate

Oxaliplatin

P

Paclitaxel

Paclitaxel Albumin-stabilized Nanoparticle Formulation

PAD

Palbociclib

Palifermin

Palonosetron Hydrochloride

Palonosetron Hydrochloride and Netupitant

Pamidronate Disodium

Panitumumab

Panobinostat

Pazopanib Hydrochloride

PCV

PEB

Pegaspargase

Pegfilgrastim

Peginterferon Alfa-2b

PEG-Intron (Peginterferon Alfa-2b)

Pembrolizumab

Pemetrexed Disodium

Perjeta (Pertuzumab)

Pertuzumab

Plerixafor

FIG. 9N

Pomalidomide

Pomalyst (Pomalidomide)

Ponatinib Hydrochloride

Portrazza (Necitumumab)

Poteligeo (Mogamulizumab-kpkc)

Pralatrexate

Prednisone

Procarbazine Hydrochloride

Procrit (Epoetin Alfa)

Proleukin (Aldesleukin)

Prolia (Denosumab)

Promacta (Eltrombopag Olamine)

Propranolol Hydrochloride

Provenge (Sipuleucel-T)

Purinethol (Mercaptopurine)

Purixan (Mercaptopurine)

Q

[No Entries]

R

Radium 223 Dichloride

Raloxifene Hydrochloride

Ramucirumab

Rasburicase

Ravulizumab-cwvz

R-CHOP

R-CVP

Recombinant Human Papillomavirus (HPV) Bivalent Vaccine

Recombinant Human Papillomavirus (HPV) Nonavalent Vaccine

Recombinant Human Papillomavirus (HPV) Quadrivalent Vaccine

Recombinant Interferon Alfa-2b

Regorafenib

FIG. 9O

Relistor (Methylnaltrexone Bromide)

R-EPOCH

Retacrit (Epoetin Alfa)

Revlimid (Lenalidomide)

Rheumatrex (Methotrexate)

Ribociclib

R-ICE

Rituxan (Rituximab)

Rituxan Hycela (Rituximab and Hyaluronidase Human)

Rituximab

Rituximab and Hyaluronidase Human

Rolapitant Hydrochloride

Romidepsin

Romiplostim

Rubidomycin (Daunorubicin Hydrochloride)

Rubraca (Rucaparib Camsylate)

Rucaparib Camsylate

Ruxolitinib Phosphate

Rydapt (Midostaurin)

S

Sancuso (Granisetron)

Sclerosol Intrapleural Aerosol (Talc)

Siltuximab

Sipuleucel-T

Somatuline Depot (Lanreotide Acetate)

Sonidegib

Sorafenib Tosylate

Sprycel (Dasatinib)

STANFORD V

Sterile Talc Powder (Talc)

Steritalc (Talc)

FIG. 9P

Stivarga (Regorafenib)
Sunitinib Malate
Sustol (Granisetron)
Sutent (Sunitinib Malate)
Sylatron (Peginterferon Alfa-2b)
Sylvant (Siltuximab)
Synribo (Omacetaxine Mepesuccinate)
T
Tabloid (Thioguanine)
TAC
Tafinlar (Dabrafenib)
Tagraxofusp-erzs
Tagrisso (Osimertinib Mesylate)
Talazoparib Tosylate
Talc
Talimogene Laherparepvec
Talzenna (Talazoparib Tosylate)
Tamoxifen Citrate
Tarabine PFS (Cytarabine)
Tarceva (Erlotinib Hydrochloride)
Targretin (Bexarotene)
Tasigna (Nilotinib)
Tavalisse (Fostamatinib Disodium)
Taxol (Paclitaxel)
Taxotere (Docetaxel)
Tecentriq (Atezolizumab)
Temodar (Temozolomide)
Temozolomide
Temsirolimus
Thalidomide
Thalomid (Thalidomide)

FIG. 9Q

Thioguanine

Thiotepa

Tibsovo (Ivosidenib)

Tisagenlecleucel

Tocilizumab

Tolak (Fluorouracil--Topical)

Topotecan Hydrochloride

Toremifene

Torisel (Temsirolimus)

Totect (Dexrazoxane Hydrochloride)

TPF

Trabectedin

Trametinib

Trastuzumab

Trastuzumab and Hyaluronidase-oysk

Treanda (Bendamustine Hydrochloride)

Trexall (Methotrexate)

Trifluridine and Tipiracil Hydrochloride

Trisenox (Arsenic Trioxide)

Tykerb (Lapatinib Ditosylate)

U

Ultomiris (Ravulizumab-cwvz)

Unituxin (Dinutuximab)

Uridine Triacetate

V

VAC

Valrubicin

Valstar (Valrubicin)

Vandetanib

VAMP

Varubi (Rolapitant Hydrochloride)

FIG. 9R

Vectibix (Panitumumab)
VeIP
Velcade (Bortezomib)
Vemurafenib
Venclexta (Venetoclax)
Venetoclax
Verzenio (Abemaciclib)
Vidaza (Azacitidine)
Vinblastine Sulfate
Vincristine Sulfate
Vincristine Sulfate Liposome
Vinorelbine Tartrate
VIP
Vismodegib
Vistogard (Uridine Triacetate)
Vitrakvi (Larotrectinib Sulfate)
Vizimpro (Dacomitinib)
Voraxaze (Glucarpidase)
Vorinostat
Votrient (Pazopanib Hydrochloride)
Vyxeos (Daunorubicin Hydrochloride and Cytarabine Liposome)
W
[No Entries]
X
Xalkori (Crizotinib)
Xeloda (Capecitabine)
XELIRI
XELOX
Xgeva (Denosumab)
Xofigo (Radium 223 Dichloride)
Xospata (Gilteritinib Fumarate)

FIG. 9S

Xtandi (Enzalutamide)

Y

Yervoy (Ipilimumab)

Yescarta (Axicabtagene Ciloleucel)

Yondelis (Trabectedin)

Z

Zaltrap (Ziv-Aflibercept)

Zarxio (Filgrastim)

Zejula (Niraparib Tosylate Monohydrate)

Zelboraf (Vemurafenib)

Zevalin (Ibritumomab Tiuxetan)

Zinecard (Dexrazoxane Hydrochloride)

Ziv-Aflibercept

Zofran (Ondansetron Hydrochloride)

Zoladex (Goserelin Acetate)

Zoledronic Acid

Zolinza (Vorinostat)

Zometa (Zoledronic Acid)

Zydelig (Idelalisib)

Zykadia (Ceritinib)

Zytiga (Abiraterone Acetate)

TRANSDERMAL PENETRANT FORMULATIONS CONTAINING CANNABIDIOL

CROSS-REFERENCE TO RELATED APPLICATIONS

This application is related to and claim priority to U.S. Provisional Application Ser. No. 62/863,236 filed Jun. 18, 2019 entitled 'Transdermal Penetrant Formulations Containing Cannabidiol." Parental non-systemic administration of buffering agents for treatment of cancer.'

FIELD OF INVENTION

This invention relates generally to methods of treatment and therapeutic uses for enhanced formulations for transdermal or topical delivery of therapeutic agents.

BACKGROUND

Cannabidiol (CBD) is a natural, non-psychoactive phytocannabinoid that occurs naturally in *cannabis* plants, including hemp. There are some 113 identified CBD's in *cannabis* plants and CBD accounts for up to 40% of the *cannabis* plant's extract. CBD is known to act on cannabinoid receptors and several other neurotransmitters in the body. Clinical research has found that CBD showed efficacy in the treatment of different diseases and syndromes including anxiety, cognition, movement disorders, and pain. The side effects of long-term use of CBD include somnolence, decreased appetite, diarrhea, fatigue, malaise, weakness, and sleeping problems. In the United States, the cannabidiol drug Epidiolex was approved by the Food and Drug Administration for treatment of two epilepsy disorders.

Current means of delivery of CBD include ingestion, inhalation, injection, and topical delivery (patches and creams). It may be supplied as CBD oil containing only CBD as the active ingredient (no included tetrahydrocannabinol [THC] or terpenes), a full-plant CBD-dominant hemp extract oil, capsules, dried *cannabis*, or as a prescription liquid solution. Topical, transdermal delivery carries several desirable advantages over other forms of delivery. For instance, injections can carry a negative stigma, requires an injection device, and has a very sharp onset peak. Inhalation similarly carries some negative stigma, requires an inhalation device or for the patient to smoke *cannabis* and has high patient to patient variability in bioavailability (general ranges from 11 to 45%). Ingestion (oral delivery) can have some issues related to first pass metabolism in the gut and liver and an issue with a large portion of the CBD failing to reach systemic circulation (bioavailability <20%) where it can have beneficial effects.

In contrast, the present inventions provide a broad range of transdermal delivery formulations comprising both creams and patches that can provide CBD to a patient through the penetration of the dermis overcoming all or a portion of the issues related to prior transdermal delivery formulations that resulted in poor bioavailability (as little as <5% bioavilability) and often no systemic uptake at all.

Therefore, there is a need for an improved transdermal delivery formulation that addresses the aforementioned drawbacks and achieves improved penetration, color, smell and stability as compared to formulations that resulted in poor bioavailability.

Aspects of the present invention fulfill these needs and provide further related advantages as described in the following summary.

SUMMARY

Aspects of the present disclosure teach certain benefits in construction and use which give rise to the exemplary advantages described below.

The present disclosure solves the problems described above by providing therapeutic agent transdermal delivery formulations with improved penetration. In at least one embodiment, disclosed herein are transdermal delivery formulations that contain a Cannabidiol. In another embodiment, disclosed herein are transdermal delivery formulations that contain a Cannabidiol and one or more other active agents.

In one aspect, disclosed herein is a transdermal delivery formulation of an active agent through the dermis of a patient, including the skin, nail or hair follicle, wherein the formulation comprises a) a transdermal delivery formulation in an amount less than about 60% w/w, comprising i. one or more phosphatides, ii. glucose, and iii. one or more fatty acids; b) water in an amount less than about 50% w/w and a Cannabidiol. In one aspect, disclosed herein is a transdermal delivery formulation of an active agent through the dermis of a patient, including the skin, nail or hair follicle, wherein the formulation comprises a) a transdermal delivery formulation in an amount less than about 60% w/w, comprising i. one or more phosphatides, ii. glucose, and iii. one or more fatty acids; b) water in an amount less than about 50% w/w and a Cannabidiol and one or more other active agents.

In another aspect, disclosed herein is a transdermal delivery formulation of an active agent through the dermis, including the skin, nail or hair follicle of a subject, wherein the formulation comprises a) a transdermal delivery formulation in an amount less than about 60% w/w, comprising i. one or more phosphatides, ii. glucose, and iii. one or more fatty acids; and b) water in an amount less than about 50% w/w, a Cannabidiol. In a further embodiment, this transdermal delivery formulation can contain one or more other active agents.

In a further aspect, disclosed herein is a transdermal delivery formulation for the treatment of a disease that comprises a Cannabidiol and one or more other active agents.

In another aspect, disclosed herein is a method to effect transdermal delivery of a Cannabidiol and in some embodiments one or more other active agents, wherein the method comprises applying to the dermis, including the skin, nails or hair follicles of a subject an effective amount of a transdermal delivery formulation containing a Cannabidiol and in some embodiments one or more other active agents, wherein the formulation comprises a) a transdermal delivery formulation in an amount less than about 60% w/w, comprising i. one or more phosphatides, glucose, and iii. one or more fatty acids; and b) water in an amount less than about 50% w/w, a Cannabidiol and in certain embodiments, one or more active agents.

Other features and advantages of aspects of the present invention will become apparent from the following more detailed description, taken in conjunction with the accompanying drawings, which illustrate, by way of example, the principles of aspects of the invention.

DESCRIPTION OF THE FIGURES

FIG. 9A-S. Listing of drugs for treatment of patients suffering from a cancer.

DETAILED DESCRIPTION

Figure 1:
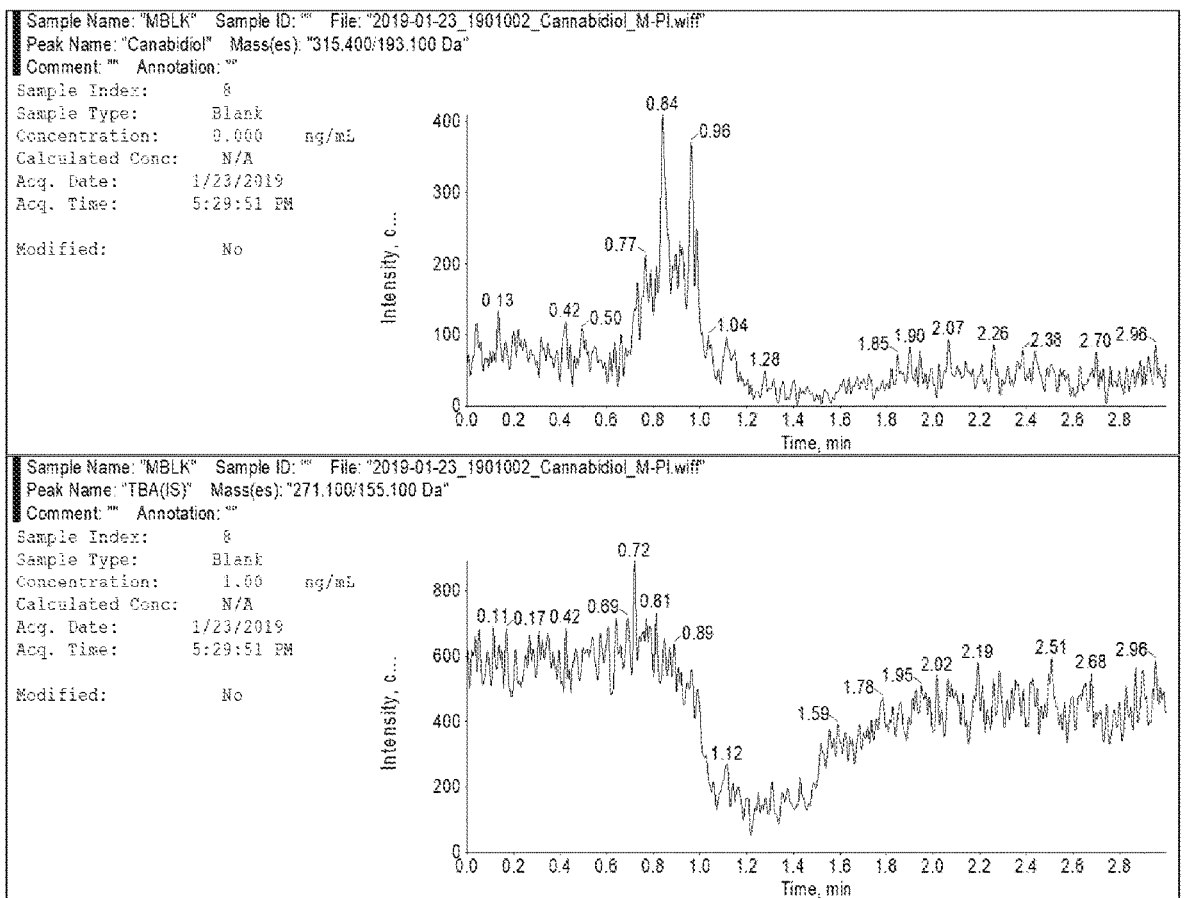
FIG. 1. Representative Chromatograms of a Matrix Blank for Cannabidiol in Mouse Plasma.
Figure 2:
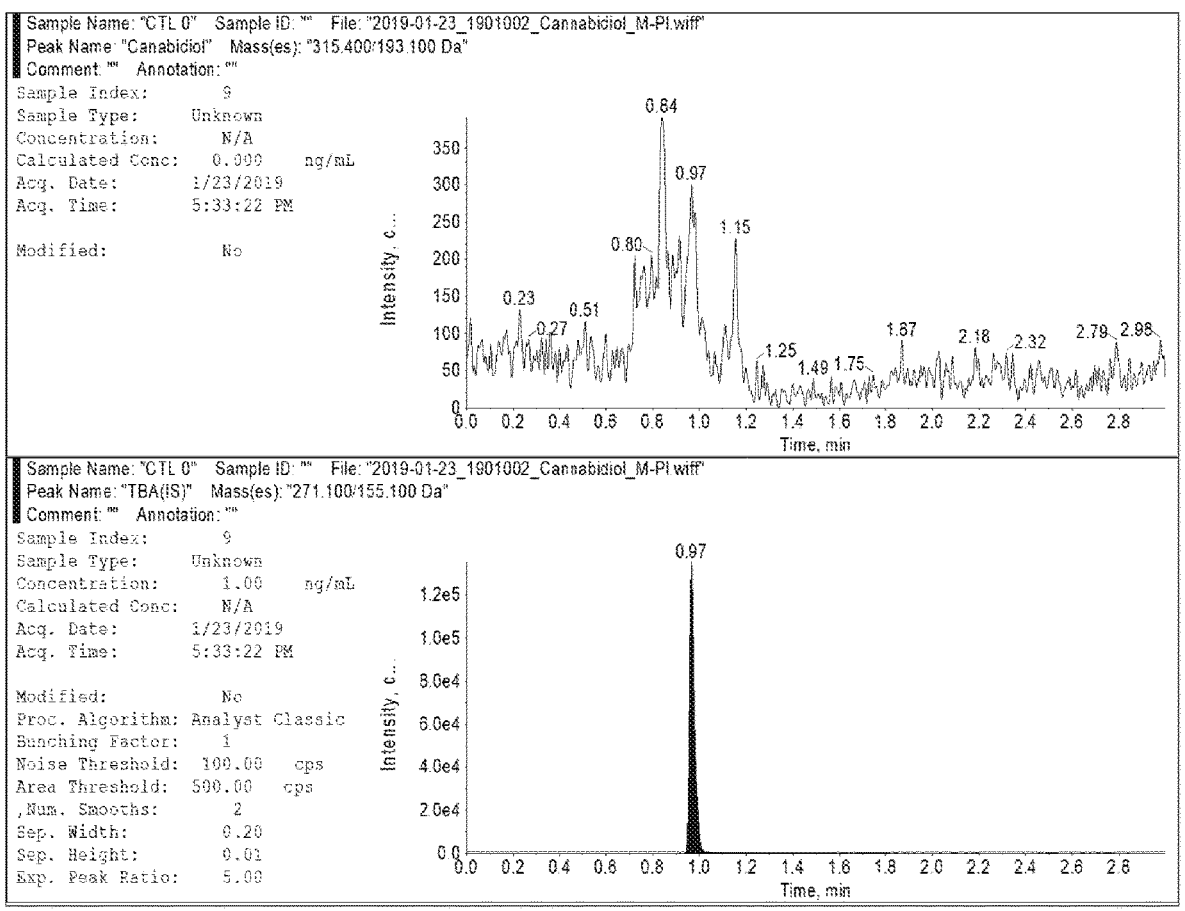
FIG. 2. Representative Chromatograms of a Control Zero for Cannabidiol in Mouse Plasma.
Figure 3:
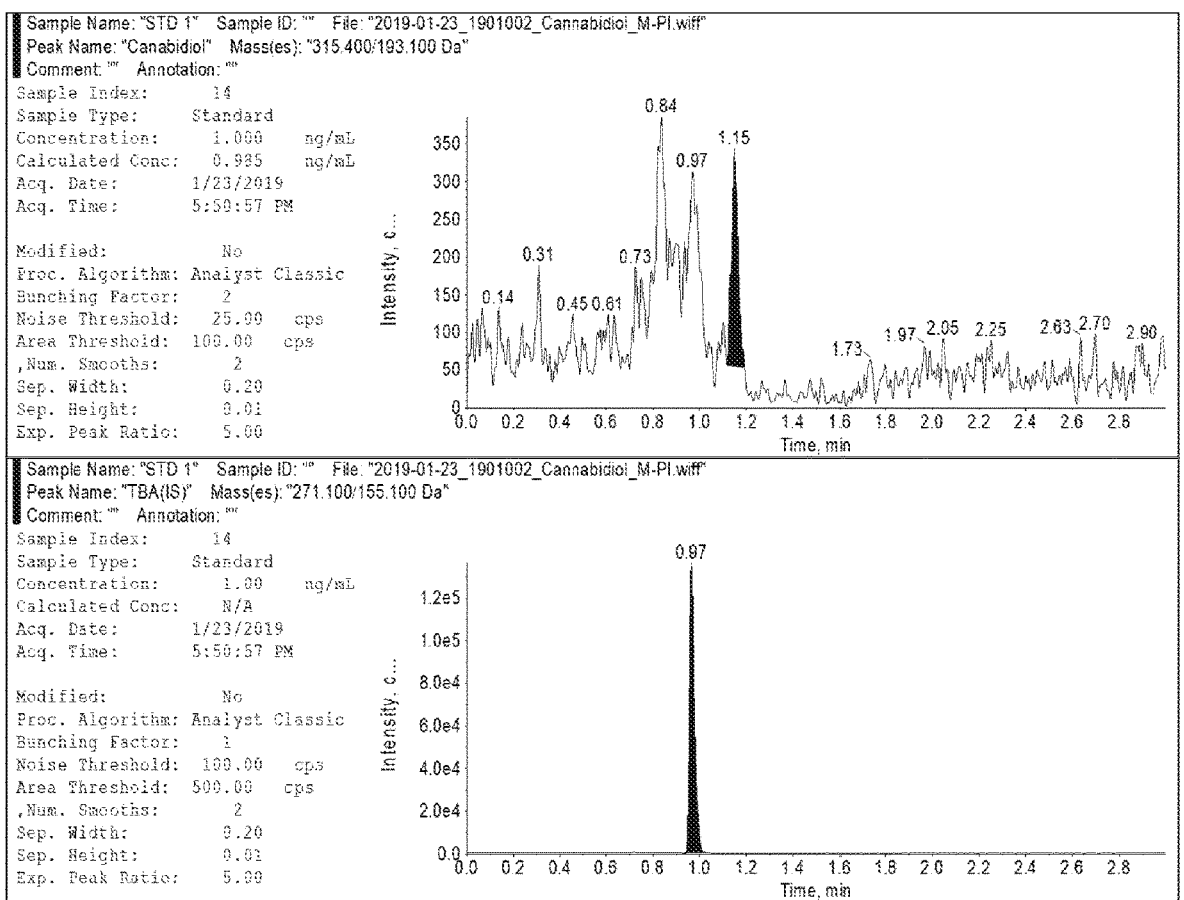
FIG. 3. Representative Chromatograms of the Lower Limit of Quantification (1 ng/mL) for Cannabidiol in Mouse Plasma.
Figure 4:
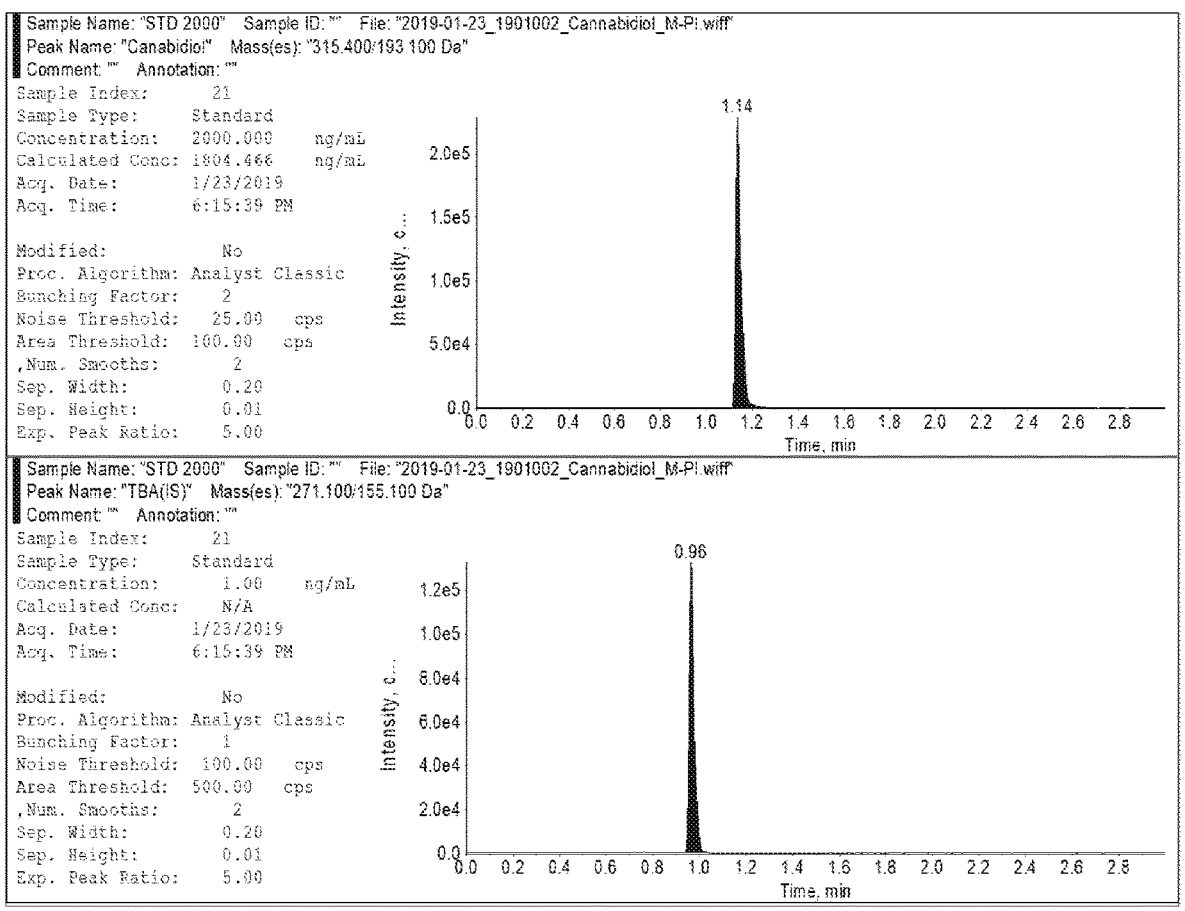
FIG. 4. Representative Chromatograms of the Upper Limit of Quantification (2000 ng/mL) for Cannabidiol in Mouse Plasma.

All numerical designations, e.g., pH, temperature, time, concentration, and molecular weight, including ranges, are to be understood as approximations in accordance with common practice in the art. When used herein, the term "about" may connote variation (+) or (−) 1%, 5% or 10% of the stated amount, as appropriate given the context. It is to be understood, although not always explicitly stated, that the reagents described herein are merely exemplary and that equivalents of such are known in the art.

Many known and useful compounds and the like can be found in Remington's Pharmaceutical Sciences (13th Ed), Mack Publishing Company, Easton, Pa.—a standard reference for various types of administration. As used herein, the term "formulation(s)" means a combination of at least one active ingredient with one or more other ingredient, also commonly referred to as excipients, which may be independently active or inactive. The term "formulation" may or may not refer to a pharmaceutically acceptable composition for administration to humans or animals and may include compositions that are useful intermediates for storage or research purposes.

As the patients and subjects of the invention method are, in addition to humans, veterinary subjects, formulations suitable for these subjects are also appropriate. Such subjects include livestock and pets as well as sports animals such as horses, greyhounds, and the like.

In an embodiment, a "pharmaceutical composition" is intended to include, without limitation, the combination of an active agent with a carrier, inert or active, in a sterile composition suitable for diagnostic or therapeutic use in vitro, in vivo or ex vivo. In one aspect, the pharmaceutical composition is substantially free of endotoxins or is non-toxic to recipients at the dosage or concentration employed.

In an embodiment, "an effective amount" refers, without limitation, to the amount of the defined component sufficient to achieve the desired chemical composition or the desired biological and/or therapeutic result. In an embodiment, that result can be the desired pH or chemical or biological characteristic, e.g., stability of the formulation. In other embodiments, the desired result is the alleviation or amelioration of the signs, symptoms, or causes of a disease, or any other desired alteration of a biological system. When the desired result is a therapeutic response, the effective amount will, without limitation, vary depending upon the specific disease or symptom to be treated or alleviated, the age, gender and weight of the subject to be treated, the dosing regimen of the formulation, the severity of the disease condition, the manner of administration and the like, all of which can be determined readily by one of skill in the art. A desired effected may, without necessarily being therapeutic, also be a cosmetic effect, in particular for treatment for disorders of the skin described herein.

In an embodiment, a "subject" of diagnosis or treatment is, without limitation, a prokaryotic or a eukaryotic cell, a tissue culture, a tissue or an animal, e.g. a mammal, including a human. Non-human animals subject to diagnosis or treatment include, for example, without limitation, a simian, a murine, a canine, a leporid, such as a rabbit, livestock, sport animals, and pets.

In an embodiment, as used herein, the terms "treating," "treatment" and the like are used herein, without limitation, to mean obtaining a desired pharmacologic and/or physiologic effect. The effect may be prophylactic in terms of completely or partially preventing a disorder or sign or symptom thereof, and/or may be therapeutic in terms of amelioration of the symptoms of the disease or infection, or a partial or complete cure for a disorder and/or adverse effect attributable to the disorder.

For purposes herein, a formulation, a formulation for transdermal delivery and a transdermal delivery formulation are each a formulation for transdermal delivery, including, the transdermal delivery of an active ingredient for the treatment of a syndrome and or a disease in an individual.

For purposes herein, the terms lecithin and lecithin organogel are used interchangeably and both refer to, include and cover a lecithin organogel that comprises any aroup of yellow-brownish fatty substances occurring in animal and plant tissues which are amphiphilic and include a mixture of one or more of glycerophospholipids including phosphatidylcholine, phosphatidylethanolamine, phosphatidylinositol, phosphatidylserine, and phosphatidic acid.

Additionally, the use of particular formulations can disrupt the balance of electrolytes and cations, including those such as the Na/K ratio. For example, the administration of formulations containing calcium carbonate can reduce the amount of sodium or other ions which can decrease the potential for reaching a hyponatremic state. Also, the use of calcium carbonate can also increase the serum levels of calcium which can reduce the amount of calcium leeched from the body by high sodium concentrations.

The formulations and methods of use provided herein take these complexities of electrolyte balance into account. One approach utilized herein in making formulations that avoid electrolyte imbalance and cation overload is to use non-metal buffers or buffers without counterions. Suitable buffering agents for these embodiments include Lysine (free base), TRIS, and IEPA.

For transdermal topical administration in particular for agents other than buffer, a suitable formulation typically involves a penetrant that enhances penetration of the skin and is, in some embodiments, composed of chemical permeation enhancers (CPEs). In some cases, it can also include peptides designed to penetrate cells i.e. cell penetrating peptides (CPPs) also known as skin penetrating peptides (SPPs). The formulation may be applied for example in the form of topical lotions, creams, and the like, as described herein.

If the active agent is a buffer, the choice of buffer system is based on the criteria of capability of buffering at a suitable pH typically between 7 and 10.5, as well as biocompatibility of the buffer system itself and the compatibility of the buffer system with the remaining components of the formulation. Conversely, the formulation is chosen to be compatible with the buffer selected; amounts of penetrants are generally less than those advantageous for therapeutic agents in general.

The present disclosure herein demonstrates transdermal drug delivery, but avoids some of the negative effects on color, smell, grittiness and stability driven by the use of lecithin organogel, and further optimizes transdermal penetration Transdermal Delivery Formulation Components Phosphatides—Soy lecithin contains about 57.5% w/w phosphatides. The primary phosphatides found in Soy Lecithin are inositol phosphatides (20.5% w/w of Soy lecithin), phosphatidylcholine (20%), and phosphatidylethanolamine (11% w/w of Soy lecithin). In some embodiments, phosphatidylcholine is used for the full amount (57.5% w/w of Soy lecithin) as it is known to aide in skin penetration. Other phosphatides include phosphatidic acid, phosphatidylserine and phosphatidylinositol.

In an embodiment, a transdermal delivery formulation contains a phosphatide in a concentration of at least 5%, at least 10%, at least 15%, at least 20%, at least 25%, at least 30%, at least 35%, at least 40%, at least 45%, at least 50%, at least 55%, at least 60%, at least 65%, at least 70% or more w/w of the transdermal delivery formulation.

Sterols—Soy lecithin contains about 2.5% w/w sterols. In some embodiments, benzyl alcohol is used in substitution of the sterol in a transdermal delivery formulation to act as a penetration enhancer. In another embodiment, a sterol is cholesterol, ergosterol, hopanoids, hydroxysteroid, phytosterol and/or other steroids.

In an embodiment, a transdermal delivery formulation contains a sterol or benzyl alcohol in a concentration of at least 1%, at least 2%, at least 3%, at least 4%, at least 5%, at least 6%, at least 7%, at least 8%, at least 9%, at least 10%, at least 15%, at least 20%, at least 25%, at least 30% or more w/w of the transdermal delivery formulation.

Carbohydrates—Soy lecithin contains about 5% w/w free carbohydrates. In some embodiments, glucose is used in substitution of a free carbohydrate to maintain the ratio of sugars in the transdermal delivery formulation disclosed herein. In another embodiment, a carbohydrate is a monosaccharide, a disaccharide, a polyol, a malto-oligosaccharide, an oligosaccharide, a starch, a polysaccharide. In a further embodiment, a carbohydrate is glucose, galactose, fructose, xylose, sucrose, lactose, maltose, trehalose, sorbitol, mannitol, maltodextrins, raffinose, stachyose, fructooligosaccharide, amylose, amylopectin, modified starches, glycogen, cellulose, hemicellulose, pectin and/or hydrocolloid.

In an embodiment, a transdermal delivery formulation contains a carbohydrate in a concentration of at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70% or more w/w of the transdermal delivery formulation.

Moisture—In some embodiments, the transdermal delivery formulation maintains the about 1% w/w of water contained in Soy lecithin.

In an embodiment, a transdermal delivery formulation contains water in a concentration of at least 0.1%, at least 0.2%, at least 0.3%, at least 0.4%, at least 0.5%, at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70% or more w/w of the transdermal delivery formulation.

Fatty acids—Soy lecithin contains about 34% w/w fatty acids, including 18-19% w/w linoleic acid, 1-2% w/w alpha-linoleic acid, 8-9% w/w oleic acid, about 5% w/w Palmitic acid, and 1-2% w/w stearic acids. In some embodiments, the fatty acids are similar to the fatty acids contained in soy lecithin. In an embodiment, alpha-linoleic is removed from the transdermal delivery formulation as it is known to oxidize and can become rancid. In some embodiments, the amount of stearic acid has been increased (i.e., enhancing with stability of the formulation) or linoleic acid (i.e., enhances skin penetration). In some embodiments, a seed oil such as purified safflower oil is used in a transdermal delivery formulation due to its similarity to the fatty acids found in Soy lecithin, its relative availability and its low cost. In some embodiments, the fatty acid content of a transdermal formulation can be adjusted with a different seed oil through the addition of smaller amounts of the fatty acids disclosed herein.

In an embodiment, a transdermal delivery formulation contains a carbohydrate in a concentration of at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70% or more w/w of the transdermal delivery formulation.

In a further embodiment, a fatty acid is a saturated or an unsaturated fatty acid. In another embodiment, an unsaturated fatty acid is myristoleic acid, palmitoleic acid, sapienic acid, oleic acid, elaidic acid, vaccenic acid, linoleic acid, linoelaidic acid, α-Linolenic acid, arachidonic acid, eicosapentaenoic acid, erucic acid and/or docosahexaenoic acid. In an embodiment, a saturated fatty acid is caprylic acid, capric acid, lauric acid, myristic acid, palmitic acid, stearic acid, arachidic acid, behenic acid, lignoceric acid and/or cerotic acid. In another embodiment, the fatty acid is a dietary fat and include duct fat, lard, tallow, butter, coconut oil, cocoa butter, palm kernel oil, palm oil, cottonseed oil, wheat germ oil, soybean oil, olive oil, corn oil, sunflower oil, safflower oil, help oil and/or canola/rapeseed oil.

In some embodiments, carotenoids are excluded from the formulations disclosed herein.

Herein we describe formulations demonstrating the replacement of lecithin organogel (i.e., Lecithin and Isopropyl Palmitate).

In an embodiment, a transdermal delivery formulation containing CBD comprises the components of Table 1:

TABLE 1

| Ingredient | Weight % |
| --- | --- |
| Phosphatidylcholine | 28.75% |
| Glucose | 2.50% |
| Benzyl Alcohol | 1.25% |
| Deionized water | 0.50% |
| Linoleic Acid | 9.75% |
| Oleic Acid | 4.38% |
| Stearic Acid | 2.88% |
| Isopropyl Palmitate | 50.00% |

In some another embodiment, a transdermal delivery formulation containing CBD comprises the components of Table 2:

TABLE 2

| Ingredient | Weight % |
| --- | --- |
| Phosphatidylcholine | 28.75% |
| Glucose | 2.50% |
| Benzyl Alcohol | 1.25% |
| Deionized water | 0.50% |
| ILinoleic Acid | 9.75% |
| Oleic Acid | 4.38% |
| Stearic Acid | 2.88% |
| Isopropyl Palmitate | 50.00% |

In an aspect, the concentration of Phosphatidylcholine in a transdermal delivery formulation is at least 10%, at least 15%, at least 20%, at least 25%, at least 28.75%, at least 30%, at least 35%, at least 40% or more. In an aspect, the concentration of Phosphatidylcholine in a transdermal delivery formulation is not more than 10%, not more than 15%, not more than 20%, not more than 25%, not more than 28.75%, not more than 30%, not more than 35%, not more than 40% or more. In an aspect, the concentration of Phosphatidylcholine in a transdermal delivery formulation is about 10%, about 15%, about 20%, about 25%, at least 28.75%, about 30%, about 35%, about 40% or more. In an aspect, the concentration of Phosphatidylcholine in a transdermal delivery formulation is from 1% to 30%, is from 2.5% to 20%, is from 4% to 15%, is from 5% to 10%, is from 10% to 40%, is from 15% to 35%, is from 20% to 30%, is from 25% to 30%, is from 28% to 29%.

In another aspect, the concentration of Glucose in a transdermal delivery formulation is at least 1%, at least 2%, at least 2.5%, at least 3%, at least 4%, at least 5%, at least 6%, at least 7%, at least 8%, at least 9% or more. In another aspect, the concentration of Glucose in a transdermal delivery formulation is about 1%, about 2%, about 2.5%, about 3%, about 4%, about 5%, about 6%, about 7%, about 8%, about 9% or more. In another aspect, the concentration of Glucose in a transdermal delivery formulation is no more than 1%, no more than 2%, no more than 2.5%, no more than 3%, no more than 4%, no more than 5%, no more than 6%, no more than 7%, no more than 8%, no more than 9% or more. In another aspect, the concentration of Glucose in a transdermal delivery formulation is from 0% to 5%, is from 0.1% to 4%, if from 0% to 2%, is from 0% to 3%, is from 1% to 10%, is from 2% to 9%, is from 2.5% to 5%, is from 1% to 3%, if from 1.5% to 2%, is from 0.5% to 2%, is from 2% to 3%, is from 3% to 8%, if from 4% to 7%, is from 5% to 6%, is from 2% to 4%, if from 1.5% to 3.55%.

In a further embodiment, the concentration of Benzyl Alcohol in a transdermal formulation is at least 0.25%, at least 0.5%, at least 0.75%, at least 1%, at least 2%, at least 2.5%, at least 3%, at least 4%, at least 5% or more. In an embodiment, the concentration of Benzyl Alcohol in a transdermal formulation is about 0.25%, about 0.5%, about 0.75%, about 1%, about 2%, about 2.5%, about 3%, about 4%, about 5% or more. In another embodiment, the concentration of Benzyl Alcohol in a transdermal formulation is at from 0.25% to 5%; from 0.5% to 4%, from 0.75% to 3%, from 1% to 2.5% or from 0.5% to 2%. In a further embodiment, the concentration of Benzyl Alcohol in a transdermal formulation is no more than 0.25%, no more than 0.5%, no more than 0.75%, no more than 1%, no more than 2%, no more than 2.5%, no more than 3%, no more than 4%, no more than 5%.

In an embodiment, the concentration of Deionized Water in a transdermal formulation is at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5% or more. In an embodiment, the concentration of Deionized Water in a transdermal formulation is about 0.1%, about 0.2%, about 0.3%, about 0.4%, about 0.5%, about 0.6%, about 0.7%, about 0.8%, about 0.9%, about 1%, about 2%, about 3%, about 4%, about 5% or more. In an embodiment, the concentration of Deionized Water in a transdermal formulation is from 0.1% to 5%, from 0.2% to 4%, from 0.3% to 3%, 0.4%-2%, 0.5% to 1%, from 0.6% to 0.9%, from 0.7% to 0.8%, from 0.4% to 1.5%, from 0.3% to 0.7%, from 7% to 80%, from 10% to 15%, from 10% to 50%, from 20% to 50%, from 25% to 75%, from 30% to 60%, from 40% to 60%, from 40% to 50%, or from 0.4% to 0.6%. In an embodiment, the concentration of Deionized Water in a transdermal formulation is no more than 0.1%, no more than 0.2%, no more than 0.3%, no more than 0.4%, no more than 0.5%, no more than 0.6%, no more than 0.7%, no more than 0.8%, no more than 0.9%, no more than 1%, no more than 2%, no more than 3%, no more than 4%, no more than 5% or more.

In an aspect, the concentration of Safflower oil, including a linoleic acid, in a transdermal delivery formulation is at least 1%, at least 5%, at least 7.5%, at least 10%, at least 11%, at least 11.06%, at least 12%, at least 13%, at least 14%, at least 15%, at least 16%, at least 17%, at least 18%, at least 19%, at least 20% or more. In an aspect, the concentration of Safflower oil in a transdermal delivery formulation is about 1%, about 5%, about 7.5%, about 10%, about 11%, about 11.06%, about 12%, about 13%, about 14%, about 15%, about 16%, about 17%, about 18%, about 19%, about 20% or more. In an aspect, the concentration of Safflower oil in a transdermal delivery formulation is from 1% to 20%, from 1% to 10%, from 1% to 15%, from 2% to 10% from 5 to 10%, from 1% to 7%, from 1% to 5% from 2% to 4%, from 5% to 19%, from 7.5% to 18%, from 10% to 17%, from 11% to 16%, from 11.06%, 12% from 11% to 12%, from 12% to 14%, from 13% to 14%, from 10% to 12%, from 10.5% to 12.5% or from 11% to 11.25%. In an aspect, the concentration of Safflower oil in a transdermal delivery formulation is no more than 1%, no more than 5%, no more than 7.5%, no more than 10%, no more than 11%, no more than 11.06%, no more than 12%, no more than 13%, no more than 14%, no more than 15%, no more than 16%, no more than 17%, no more than 18%, no more than 19%, no more than 20%, no more than or more.

In a further aspect, the concentration of Oleic Acid in a transdermal delivery formulation is at least 1%, at least 2%, at least 3%, at least 3.65%, at least 4%, at least 5%, at least 6%, at least 7%, at least 8%, at least 9%, at least 10% or more. In a further aspect, the concentration of Oleic Acid in a transdermal delivery formulation is about 1%, about 2%, about 3%, about 3.65%, about 4%, about 5%, about 6%, about 7%, about 8%, about 9%, about 10% or more. In a further aspect, the concentration of Oleic Acid in a transdermal delivery formulation is no more than 1%, no more than 2%, no more than 3%, no more than 3.65%, no more than 4%, no more than 5%, no more than 6%, no more than 7%, no more than 8%, no more than 9%, no more than 10% or more. In another aspect, the concentration of Oleic Acid in a transdermal formulation is from 1% to 10%, from 2% to 9%, from 2% to 3%, from 3% to 4%, from 3% to 8%, from 4% to 7%, from 5% to 6%, from 2 to 2.5%, from 0.2% to 10%, from 0.2% to 7.5%, from 0.2% to 5%, from 1% to 7.5%, from 2 to 5%, from 3% to 5%, or from 2.5% to 4%.

In another aspect, the concentration of Stearic Acid in a transdermal formulation is at least 1%, at least 2%, at least 2.34%, at least 3%, at least 4%, at least 5%, at least 6%, at least 7%, at least 8%, at least 9%, at least 10% or more. In another aspect, the concentration of Stearic Acid in a transdermal formulation is no more than 1%, no more than 2%, no more than 2.34%, no more than 3%, no more than 4%, no more than 5%, no more than 6%, no more than 7%, no more than 8%, no more than 9%, no more than 10% or more. In another aspect, the concentration of Stearic Acid in a transdermal formulation is about 1%, about 2%, about 2.34%, about 3%, about 4%, about 5%, about 6%, about 7%, about 8%, about 9%, about 10% or more. In another aspect, the concentration of Stearic Acid in a transdermal formulation is from 1% to 10%, from 2% to 9%, from 2% to 3%, from 2.34% to 2.5%, from 3% to 8%, from 4% to 7%, from 5% to 6%, from 0.2% to 10%, from 0.2% to 7% from 0.2% to 5%, from 0.2% to 3%, from 1% to 8%, from 3% to 7%, from 4% to 6%, from 2% to 7% or from 1.5% to 2.5%.

In an aspect, the concentration of Isopropyl Palmitate in a transdermal formulation is at least 10%, at least 20%, at least 25%, at least 30%, at least 40%, at least 45%, at least 50%, at least 55%, at least 60%, at least 65%, at least 70%, at least 75% or more. In an aspect, the concentration of Isopropyl Palmitate in a transdermal formulation is about 10%, about 20%, about 25%, about 30%, about 40%, about 45%, about 50%, about 55%, about 60%, about 65%, about 70%, about 75% or more. In an aspect, the concentration of Isopropyl Palmitate in a transdermal formulation is no more than 10%, no more than 20%, no more than 25%, no more than 30%, no more than 40%, no more than 45%, no more than 50%, no more than 55%, no more than 60%, no more than 65%, no more than 70%, no more than 75% or more. In an aspect, the concentration of Isopropyl Palmitate in a transdermal formulation is from 10% to 75%, from 3% to 30%, from 5% to 35%, from 5% to 30%, from 7% to 25%, from 10% to 20% form 10% to 25% from 7% to 35%, from 7% to 20%, from 15% to 25%, from 25% to 20%, from 20% to 25%, from 20% to 70%, from 25% to 65%, from 30% to 60%, from 40% to 55%, from 45% to 50%, from 40% to 60%, from 45% to 55% or from 47% to 53%.

In an embodiment, the concentration of CBD in a transdermal formulation is 10 mg/kg, 15 mg/kg, 20 mg/kg, 25 mg/kg, 30 mg/kg, 35 mg/kg, 40 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 190 mg/kg, 195 mg/kg, 200 mg/kg, 205 mg/kg, 210 mg/kg, 215 mg/kg, 220 mg/kg, 225 mg/kg, 230 mg/kg, 235 mg/kg, 240 mg/kg, 245 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg or greater than 500 mg/kg. In an aspect, the concentration of CBD in a transdermal formulation is from 0.1% to 10%, from 0.5% to 8%, from 1% to 7%, from 1.5% to 6%, from 2% to 5%, from 2.5% to 4%, from 2% to 4%, from 1.5% to 4%, from 1.5% to 5%, from 2% to 5%, from 2% to 6%, from 2% to 3%, from 2.25% to 2.75% or from 2.4% to 2.6%.

In an embodiment, the concentration of CBD in a transdermal formulation is at least 10 mg/kg, 15 mg/kg, 20 mg/kg, 25 mg/kg, 30 mg/kg, 35 mg/kg, 40 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 190 mg/kg, 195 mg/kg, 200 mg/kg, 205 mg/kg, 210 mg/kg, 215 mg/kg, 220 mg/kg, 225 mg/kg, 230 mg/kg, 235 mg/kg, 240 mg/kg, 245 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg or greater than 500 mg/kg.

In an embodiment, the concentration of CBD in a transdermal formulation is about 10 mg/kg, 15 mg/kg, 20 mg/kg, 25 mg/kg, 30 mg/kg, 35 mg/kg, 40 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 190 mg/kg, 195 mg/kg, 200 mg/kg, 205 mg/kg, 210 mg/kg, 215 mg/kg, 220 mg/kg, 225 mg/kg, 230 mg/kg, 235 mg/kg, 240 mg/kg, 245 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg or greater than 500 mg/kg.

In an embodiment, the concentration of CBD in a transdermal formulation is no more than 10 mg/kg, 15 mg/kg, 20 mg/kg, 25 mg/kg, 30 mg/kg, 35 mg/kg, 40 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 125 mg/kg, 130 mg/kg, 135 mg/kg, 140 mg/kg, 145 mg/kg, 150 mg/kg, 155 mg/kg, 160 mg/kg, 165 mg/kg, 170 mg/kg, 175 mg/kg, 180 mg/kg, 190 mg/kg, 195 mg/kg, 200 mg/kg, 205 mg/kg, 210 mg/kg, 215 mg/kg, 220 mg/kg, 225 mg/kg, 230 mg/kg, 235 mg/kg, 240 mg/kg, 245 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg or greater than 500 mg/kg.

Certain components or ingredients of transdermal delivery formulation provided herein may be supplemented with components described in greater detail in the inventor's related applications mentioned above, including U.S. application Ser. No. 16/132,358 filed Sep. 14, 2018, entitled 'Methods and Formulations For Transdermal Administration Of Buffering Agents', International Patent Application No. PCT/US18/51250 filed Sep. 14, 2018, entitled 'Methods of Administration and Treatment', and International Patent Application PCT/US18/28017 by Bruce Sand filed Apr. 17, 2018, entitled 'Parental non-systemic administration of buffering agents for inhibiting metastasis of solid tumors, hyperpigmentation and gout', all incorporated by reference in their entirety herein.

A transdermal delivery formulation of the disclosure may be prepared in a number of ways. Typically, the components of a transdermal delivery formulation are simply mixed together in the required amounts.

In some embodiments, the CBD is formulated with Aveeno® moisturizers, cream, oils, lotions; Jergens® moisturizers, cream, oils, lotions; Honest Company® moisturizers, cream, oils, lotions; Dermologica® moisturizers, cream, oils, lotions; or St. Ives™ moisturizers, cream, oils, lotions. In some embodiments, the commercial lotions, moisturizers, etc. are formulated with the ketone component in an amount between about 10-60% w/w or at least 10% w/w, at least 20% w/w, at least 30% w/w, at least 40% w/w, at least 50% w/w, at least 60% w/w, at least 75% w/w or more.

The transdermal delivery formulation is a multi-component mixture, whereby the particular concentrations of the penetration enhancers are informed in part by the particle size of the CBD component. The formulation enables the CBD component to become bio-available to the target site within minutes of topical administration. In some embodiments, the transdermal delivery formulation comprises an alcohol in an amount less than 5% w/w of the formulation.

Subjects of the disclosure herein, in addition to humans, include veterinary subjects, wherein formulations suitable for these subjects are also appropriate. Such subjects include livestock and pets as well as sports animals such as horses and greyhounds.

A transdermal delivery formulation comprise mixtures wherein the components interact synergistically and induce skin permeation enhancements better than that induced by the individual components. Synergies between chemicals can be exploited to design potent permeation enhancers that overcome the efficacy limitations of single enhancers. Several embodiments disclosed herein utilize one or more distinct permeation enhancers.

For topical administration, and in particular transdermal administration, a transdermal delivery formulation will comprise penetrants including either or both chemical penetrants (CPEs) and peptide-based cellular penetrating agents (CPPs) that encourage transmission across the dermis and/or across membranes including cell membranes, as would be the case in particular for administration by suppository or intranasal administration, but for transdermal administration as well. In some embodiments, suitable penetrants include those that are described in the above-referenced US2009/0053290 ('290), WO2014/209910 ('910), and WO2017/127834. In addition to transdermal delivery formulations with penetrants, transdermal delivery can be affected by mechanically disrupting the surface of the skin to encourage penetration, or simply by supplying the formulation applied to the skin under an occlusive patch.

Alternatively, the transdermal delivery formulation comprises a completion component as well as one or more electrolytes sufficient to impart viscosity and viscoelasticity, one or more surfactants and an alcohol. The completion component can be a polar liquid, a non-polar liquid or an amphiphilic substance. The penetrant may further comprise a keratinolytic agent effective to reduce thiol linkages, disrupt hydrogen bonding and/or effect keratin lysis and/or a cell penetrating peptide (sometimes referred to as a skin-penetrating peptide) and/or a permeation enhancer.

Suitable gelling components also include isopropyl palmitate, ethyl laurate, ethyl myristate and isopropyl myristate. In some embodiments, a transdermal delivery formulation comprises a gelling agent in an amount less than 5% w/w of a transdermal delivery formulation. Certain hydrocarbons, such as cyclopentane, cyclooctane, trans-decalin, trans-pinane, n-pentane, n-hexane, n-hexadecane may also be used. In some embodiments, the transdermal delivery formulation comprises a mixture of xanthan gum, sclerotium gum, pullulan, or a combination thereof in an amount less than 2% w/w, 5% w/w, or 10% w/w of the formulation. In some embodiments, a transdermal delivery formulation comprises Siligel™ in an amount between about 1-5% w/w or 5-15% w/w, or an equivalent mixture of xanthan gum, sclerotium gum, and pullulan. In some embodiments, a transdermal delivery formulation comprises a mixture of caprylic triglycerides and capric triglycerides in amount less than 2% w/w, 8% w/w, or 10% w/w of the formulation. In some embodiments, a transdermal delivery formulation comprises Myritol® 312 in an amount between about 0.5-10% w/w, or an equivalent mixture of caprylic triglycerides and capric triglycerides.

In some embodiments, a transdermal delivery formulation is in an amount between about 10-90% w/w or 10-50% w/w of the formulation or at least 10% w/w, at least 20% w/w, at least 30% w/w, at least 40% w/w, at least 50% w/w, at least 60% w/w, at least 70% w/w, at least 80% w/w, at least 90% w/w or at least 95% w/w. In some embodiments, a transdermal delivery formulation comprises phosphatidyl choline in amount less than 7% w/w, less than 8% w/w, less than 9% w/w, less than 10% w/w, less than 11% w/w, less than 12% w/w, less than 13% w/w, less than 14% w/w, less than 15% w/w, less than 16% w/w, less than 17% w/w or less than 18% w/w of the formulation. In some embodiments, a transdermal delivery formulation comprises a phospholipid in amount less than 20% w/w, less than 30% w/w, less than 40% w/w, less than or 50% w/w of the formulation. In some embodiments, a transdermal delivery formulation comprises a mixture of tridecane and undecane in amount less than 2% w/w, 3% w/w, 4% w/w, 5% w/w, 6% w/w, 7% w/w, or 8% w/w of the formulation. In some embodiments, the formulation comprises Cetiol Ultimate® in an amount less than about 2% w/w, 3% w/w, 4% w/w, 5% w/w, 6% w/w, 7% w/w, 8% w/w, 9% w/w, or 10% w/w, or an equivalent mixture of tridecane and undecane. In some embodiments, a transdermal delivery formulation comprises cetyl alcohol in amount less than 2% w/w, 3% w/w, 4% w/w, 5% w/w, 6% w/w, 7% w/w, 8% w/w, 9% w/w, or 10% w/w of the formulation. In some embodiments, the formulation comprises benzyl alcohol in an amount less than about 2% w/w, 3% w/w, 4% w/w, 5% w/w, 6% w/w, 7% w/w, 8% w/w, 9% w/w, or 10% w/w. In some embodiments, a transdermal delivery formulation comprises stearic acid in an amount less than 2% w/w, 3% w/w, 4% w/w, 5% w/w, 6% w/w, 7% w/w, 8% w/w, 9% w/w, or 10% w/w of the formulation. In some embodiments, the transdermal delivery formulation comprises phosphatidylcholine, hydrogenated phosphatidylcholine, phosphatidylserine, phosphatidylethanolamine, phosphatidylinositol, one or more phosphatides, one or more Inositol phosphatides, or combinations thereof, in amount less than 30% w/w or in amount less than 12% w/w of the formulation.

An additional component in a transdermal delivery formulation of the disclosure is an alcohol. Benzyl alcohol and ethanol are illustrated in the Examples. In particular, derivatives of benzyl alcohol which contain substituents on the benzene ring, such as halo, alkyl and the like. The weight percentage of benzyl or other related alcohol in the final composition is 0.5-20% w/w, and again, intervening percentages such as 1% w/w, 2% w/w, 53% w/w, 4% w/w, 5% w/w, 6% w/w, 7% w/w, 8% w/w, 9% w/w, or 10% w/w, and other intermediate weight percentages are included. Due to the aromatic group present in a transdermal delivery formulation such as benzyl alcohol, the molecule has a polar end (the alcohol end) and a non-polar end (the benzene end). This enables the agent to dissolve a wider variety of transdermal delivery formulation components.

In some embodiments, as noted above, the performance of a transdermal delivery formulation is further improved by including a nonionic detergent and polar gelling agent or including a powdered surfactant. In both aqueous and anhydrous forms of the composition, detergents, typically nonionic detergents are added. In general, the nonionic detergent should be present in an amount between about 1% w/w to 30% w/w of a transdermal delivery formulation. Typically, in the compositions wherein a transdermal delivery formulation is topped off with a polar or aqueous solution containing detergent, the amount of detergent is relatively low—e.g., 2-25% w/w, or 5-15% w/w or 7-12% w/w of a transdermal delivery formulation. However, in compositions that are essentially anhydrous and are topped-off by powdered detergent, relatively higher percentages are usually used—e.g., 20-60% w/w.

In some embodiments, a transdermal delivery formulation further comprises a detergent portion in an amount between about 1 to 70% w/w or 1-60% w/w of a transdermal delivery formulation. In some embodiments, the nonionic detergent provides suitable handling properties whereby the formulations are gel-like or creams at room temperature. To exert this effect, the detergent, typically a poloxamer, is present in an amount between about 2-12% w/w of a transdermal delivery formulation, preferably between about 5-25% w/w in polar formulations. In the anhydrous forms of the compositions, the detergent is added in powdered or micronized form to bring the composition to 100% and higher amounts are used. In compositions with polar constituents, rather than bile salts, the nonionic detergent is added as a solution to bring the composition to 100%. If smaller amounts of detergent solutions are needed due to high levels of the remaining components, more concentrated solutions of the nonionic detergent are employed. Thus, for example, the percent detergent in the solution may be 10% to 40% or 20% or 30% and intermediate values depending on the percentages of the other components.

Suitable nonionic detergents include poloxamers such as the non-ionic surfactant Pluronic® and any other surfactant characterized by a combination of hydrophilic and hydrophobic moieties. Poloxamers are triblock copolymers of a central hydrophobic chain of polyoxypropylene flanked by two hydrophilic chains of polyethyleneoxide. Other nonionic surfactants include long chain alcohols and copolymers of hydrophilic and hydrophobic monomers where blocks of hydrophilic and hydrophobic portions are used.

In some embodiments, a transdermal delivery formulation also contains surfactant, typically, nonionic surfactant at 2-25% w/w of a transdermal delivery formulation along with a polar solvent wherein the polar solvent is present in an amount at least in molar excess of the nonionic surfactant. In these embodiments, typically, the composition comprises the above-referenced amounts of a transdermal delivery formulation and benzyl alcohol along with a ketone component with a sufficient amount of a polar solution, typically an aqueous solution or polyethylene glycol solution that itself contains 10%-40% of surfactant, typically nonionic surfactant to bring the composition to 100%.

Other examples of surfactants include polyoxyethylated castor oil derivatives such as HCO-60 surfactant sold by the HallStar Company; nonoxynol; octoxynol; phenylsulfonate; poloxamers such as those sold by BASF as Pluronic® F68, Pluronic® F127, and Pluronic® L62; polyoleates; Rewopal® HV10, sodium laurate, sodium lauryl sulfate (sodium dodecyl sulfate); sodium oleate; sorbitan dilaurate; sorbitan dioleate; sorbitan monolaurate such as Span® 20 sold by Sigma-Aldrich; sorbitan monooleates; sorbitan trilaurate; sorbitan trioleate; sorbitan monopalmitate such as Span® 40 sold by Sigma-Aldrich; sorbitan stearate such as Span® 85 sold by Sigma-Aldrich; polyethylene glycol nonylphenyl ether such as Synperonic® NP sold by Sigma-Aldrich; p-(1,1,3,3-tetramethylbutyl)-phenyl ether sold as Triton™ X-100 sold by Sigma-Aldrich; and polysorbates such as polyoxyethylene (20) sorbitan monolaurate sold as Tween® 20, polysorbate 40 (polyoxyethylene (20) sorbitan monopalmitate) sold as Tween® 40, polysorbate 60 (polyoxyethylene (20) sorbitan monostearate) sold as Tween® 60, polysorbate 80 (polyoxyethylene (20) sorbitan monooleate) sold as Tween® 80, and polyoxyethylenesorbitan trioleate sold as Tween® 85 by Sigma-Aldrich. The weight percentage range of nonionic surfactant is in the range of 3% w/w-15% w/w, and again includes intermediate percentages such as 5% w/w, 7% w/w, 10% w/w, 12% w/w, and the like. In some embodiments, the detergent portion comprises a nonionic surfactant in an amount between about 1-30% w/w of the formulation; and a polar solvent in an amount less than 5% w/w of the formulation. In some embodiments, the nonionic surfactant is a poloxamer and the polar solvent is water, an alcohol, or a combination thereof. In some embodiments, the detergent portion comprises poloxamer, propylene glycol, glycerin, ethanol, 50% w/v sodium hydroxide solution, or a combination thereof. In some embodiments, the detergent portion comprises glycerin in an amount less than 3% w/w of the formulation.

In the presence of a polar gelling agent, such as water, glycerol, ethylene glycol or formamide, a micellular structure is also often achieved. Typically, the polar agent is in molar excess of the nonionic detergent. The inclusion of the nonionic detergent/polar gelling agent combination results in a more viscous and cream-like or gel-like formulation which is suitable for application directly to the skin. This is typical of the aqueous forms of the composition.

In some embodiments other additives are included such as a gelling agent, a dispersing agent and a preservative. An example of a suitable gelling agent is hydroxypropylcellulose, which is generally available in grades from viscosities of from about 5 cps to about 25,000 cps such as about 1500 cps. All viscosity measurements are assumed to be made at room temperature unless otherwise stated. The concentration of hydroxypropylcellulose may range from about 1 % w/w to about 2% w/w of the composition. Other gelling agents are known in the art and can be used in place of, or in addition to hydroxypropylcellulose. An example of a suitable dispersing agent is glycerin. Glycerin is typically included at a concentration from about 5% w/w to about 25% w/w of the composition. A preservative may be included at a concentration effective to inhibit microbial growth, ultraviolet light and/or oxygen-induced breakdown of composition components, and the like. When a preservative is included, it may range in concentration from about 0.01% w/w to about 1.5% w/w of the composition.

Additional components that may also be included in a transdermal delivery formulation are fatty acids, terpenes, lipids, and cationic, and anionic detergents. In some embodiments, a transdermal delivery formulation further comprises tranexamic acid in an amount less than 2% w/w, 5% w/w, or 10% w/w of the formulation. In some embodiments, a transdermal delivery formulation further comprises a polar solvent in an amount less than 2% w/w, 5% w/w, 10% w/w, or 20% w/w of the transdermal delivery formulation. In some embodiments, a transdermal delivery formulation further comprises a humectant, an emulsifier, an emollient, or a combination thereof. In some embodiments, a transdermal delivery formulation further comprises almond oil in an amount less than about 5% w/w. In some embodiments, a formulation further comprises a mixture of thermoplastic polyurethane and polycarbonate in an amount less than about 5% w/w. In some embodiments, a transdermal delivery formulation further comprises phosphatidylethanolamine in an amount less than about 5% w/w. In some embodiments, a transdermal delivery formulation further comprises an inositol phosphatide in an amount less than about 5% w/w.

Other solvents and related compounds that may be used in some embodiments include acetamide and derivatives, acetone, n-alkanes (chain length between 7 and 16), alkanols, diols, short chain fatty acids, cyclohexyl-1,1-dimethylethanol, dimethyl acetamide, dimethyl formamide, ethanol, ethanol/d-limonene combination, 2-ethyl-1,3-hexanediol, ethoxydiglycol (Transcutol® by Gattefosse, Lyon, France), glycerol, glycols, lauryl chloride, limonene N-methylformamide, 2-phenylethanol, 3-phenyl-1-propanol, 3-phenyl-2-propen-1-ol, polyethylene glycol, polyoxyethylene sorbitan monoesters, polypropylene glycol 425, primary alcohols (tridecanol), 1,2-propane diol, butanediol, $C_3$-$C_6$ triols or their mixtures and a polar lipid compound selected from $C_{16}$ or $C_{18}$ monounsaturated alcohol, $C_{16}$ or $C_{18}$ branched saturated alcohol and their mixtures, propylene glycol, sorbitan monolaurate sold as Span® 20 by Sigma-Aldrich, squalene, triacetin, trichloroethanol, trifluoroethanol, trimethylene glycol and xylene.

Fatty alcohols, fatty acids, fatty esters, are bilayer fluidizers that may be used in some embodiments. Examples of suitable fatty alcohols include aliphatic alcohols, decanol, lauryl alcohol (dodecanol), unolenyl alcohol, nerolidol, 1-nonanol, n-octanol, and oleyl alcohol. Examples of suitable fatty acid esters include butyl acetate, cetyl lactate, decyl N,N-dimethylamino acetate, decyl N,N-dimethylamino isopropionate, diethyleneglycol oleate, diethyl sebacate, diethyl succinate, diisopropyl sebacate, dodecyl N,N-dimethyamino acetate, dodecyl (N,N-dimethylamino)-butyrate, dodecyl N,N-dimethylamino isopropionate, dodecyl 2-(dimethyamino) propionate, E0-5-oleyl ether, ethyl acetate, ethylaceto acetate, ethyl propionate, glycerol monoethers, glycerol monolaurate, glycerol monooleate, glycerol monolinoleate, isopropyl isostearate, isopropyl linoleate, isopropyl myristate, isopropyl myristate/fatty acid monoglyceride combination, isopropyl palmitate, methyl acetate, methyl caprate, methyl laurate, methyl propionate, methyl valerate, 1-monocaproyl glycerol, monoglycerides (medium chain length), nicotinic esters (benzyl), octyl acetate, octyl N,N-dimethylamino acetate, oleyl oleate, n-pentyl N-acetylprolinate, propylene glycol monolaurate, sorbitan dilaurate, sorbitan dioleate, sorbitan monolaurate, sorbitan monolaurate, sorbitan trilaurate, sorbitan trioleate, sucrose coconut fatty ester mixtures, sucrose monolaurate, sucrose monooleate, tetradecyl N.N-dimethylamino acetate. Examples of suitable fatty acid include alkanoic acids, caprid acid, diacid, ethyloctadecanoic acid, hexanoic acid, lactic acid, lauric acid, linoelaidic acid, linoleic acid, linolenic acid, neodecanoic acid, oleic acid, palmitic acid, pelargonic acid, propionic acid, and vaccenic acid. Examples of suitable fatty alcohol ethers include a-monoglyceryl ether, E0-2-oleyl ether, E0-5-oleyl ether, E0-10-oleyl ether, ether derivatives of polyglycerols and alcohols, and (1-0-dodecyl-3-O-methyl-2-O-(2',3'-dihydroxypropyl glycerol).

Examples of completing agents that may be used in some embodiments include β- and γ-cyclodextrin complexes, hydroxypropyl methylcellulose (e.g., Carbopol® 934), liposomes, naphthalene diamide diimide, and naphthalene diester diimide.

One or more anti-oxidants may be included, such as vitamin C, vitamin E, proanthocyanidin and a-lipoic acid typically in concentrations of 0.1%-2.5% w/w.

In some applications, it is desirable to adjust the pH of a transdermal delivery formulation to assist in permeation or to adjust the nature of the ketone component and/or of the target compounds in the subject. In some instances, the pH is adjusted to a level of pH 9-11 or 10-11 which can be done by providing appropriate buffers or simply adjusting the pH with base.

In some applications, in particular when a transdermal delivery formulation includes an anesthetic, epinephrine or an alternate vasoconstrictor, such as phenylephrine or epinephrine sulfate may be included in the formulation if a stabilizing agent is present. Otherwise, the epinephrine should be administered in tandem since epinephrine is not stable at alkali pH.

Preservatives like antioxidants e.g., ascorbic acid or a-lipoic acid and antibacterial agents may be included. Other components apart from therapeutically active ingredients and components that are the primary effectors of dermal penetration may include those provided for aesthetic purposes such as menthol or other aromatics, and components that affect the physical state of the composition such as emulsifiers, for example, Durosoft® (which is a mixture of thermoplastic polyurethane and polycarbonate). Typically, these ingredients are present in very small percentages of the compositions. It is understood that these latter ancillary agents are neither therapeutically ingredients nor are they components that are primarily responsible for penetration of the skin. The components that primarily effect skin penetration have been detailed as described above. However, some of these substances have some capability for effecting skin penetration. See, for example, Kunta, J. R. et al, *J. Pharm. Sci.* (1997) 86:1369-1373, describing penetration properties of menthol.

The application method is determined by the nature of the treatment but may be less critical than the nature of the formulation itself. If the application is to a skin area, it may be helpful in some instances to prepare the skin by cleansing or exfoliation. In some instances, it is helpful to adjust the pH of the skin area prior to application of a transdermal delivery formulation itself. The application of a transdermal delivery formulation may be by simple massaging onto the skin or by use of devices such as syringes or pumps. Patches could also be used. In some cases, it is helpful to cover the area of application to prevent evaporation or loss of a transdermal delivery formulation.

Where the application area is essentially skin, it is helpful to seal-off the area of application subsequent to supplying a transdermal delivery formulation and allowing the penetration to occur so as to restore the skin barrier. A convenient way to do this is to apply a composition comprising linoleic acid which effectively closes the entrance pathways that were provided by the penetrants of the invention. This application, too, is done by straightforward smearing onto the skin area or can be applied more precisely in measured amounts.

In an embodiment, a transdermal delivery formulation containing CBD comprises the components of Table 3:

TABLE 3

| Ingredient | Weight Percent (%) |
| --- | --- |
| Lecithin | 9.03% |
| Cetyl Alcohol | 4.82% |
| Isopropyl Palmitate | 7.95% |
| Liponate GC | 3.27% |
| Crystalline Cannabidiol | 2.50% |
| Pluronic Powder | 4.65% |
| Magnesium Chloride | 1.03% |
| Deionized Water | 59.65% |
| Glycerine | 0.53% |
| Propylene Glycol | 2.19% |
| Durosoft PK-SG | 1.13% |
| Ethanol | 1.13% |
| Benzyl Alcohol | 1.09% |
| Limonene | 1.03% |
| Total | 100.00% |

In an embodiment, a transdermal delivery formulation containing CBD comprises the components of Table 4:

TABLE 4

| Ingredient | Weight Percent (%) |
| --- | --- |
| Deionized Water | 38.41% |
| Dextrose Anhydrous | 0.65% |
| Phospholipon 90G | 7.47% |
| Isopropyl Palmitate | 13.00% |
| Benzyl Alcohol | 1.36% |
| Stearic Acid | 0.75% |
| Linoleic Acid | 2.53% |
| Oleic Acid | 1.14% |
| Limonene | 1.00% |
| Crystalline Cannabidiol | 2.50% |
| Durosoft PK-SG | 1.04% |
| 30% Pluronic Gel (Dyve) | 30.15% |
| Total | 100.00% |

In an embodiment, a transdermal delivery formulation containing CBD comprises the components of Table 5:

TABLE 5

| Ingredient | Weight Percent (%) |
| --- | --- |
| Deionized Water | 38.40% |
| Dextrose Anhydrous | 0.65% |
| Phospholipon 90G | 7.47% |
| Isopropyl Palmitate | 13.00% |
| Benzyl Alcohol | 1.36% |
| Stearic Acid | 0.61% |
| Safflower Oil | 2.87% |
| Oleic Acid | 0.95% |
| Limonene | 1.00% |
| Crystalline Cannabidiol | 2.50% |
| Durosoft PK-SG | 1.04% |
| 30% Pluronic Gel (Dyve) | 30.15% |

CBD can be used for the treatment of multiple diseases. These diseases include, fibromyalgia, epilepsy, mental health diseases (including schizophrenia, post-traumatic stress and anxiety), pain, severe pain, chronic neuropathic pain, autism, alcoholism, cancer, seizures, crohn's disease, multiple sclerosis, AIDS, HIV, Amyotrohic Lateral Sclerosis (ALS), Parkinson's disease, cognition, sedation, spasms/seizures, inflammation and ulcerative colitis.

In an embodiment, the transdermal delivery formulation used to treat a disease comprises a Cannabidiol and one or more other active agents.

In an embodiment, the transdermal delivery formulation comprises a Cannabidiol and an additional active agent for the treatment of cancer.

In an embodiment, the transdermal delivery formulation comprises a Cannabidiol and an additional active agent for the treatment of cancer that is selected from those set forth in FIG. 9A-S.

In an embodiment, the transdermal delivery formulation comprises a Cannabidiol and an additional active agent for the treatment for crohn's disease, including one or more of the following, adalimumab, infliximab, a steroid, immunosuppressants, azathioprine, mercaptopurine or methotrexate.

In an embodiment, the transdermal delivery formulation comprises a Cannabidiol and an additional active agent for the treatment of multiple sclerosis, including one or more of the following, Natalizumab (Tysabri), interferon beta-1a, interferon beta-1b, Glatiramer (Copaxone, Glatopa), Teriflunomide (Aubagio), Fingolimod (Gilenya), Dimethyl fumerate (Tecfidera), Ocrelizumab (Ocrevus), Alemtuzumab (Lemtrada), mitoxantrone (Novantrone), steroids, methylprednisolone, prednisone, ACTH or plasma exchange.

In an embodiment, the transdermal delivery formulation comprises a Cannabidiol and an additional active agent for the treatment of AIDS and HIV, including one or more of the following, Abacavir, Didanosine, Emtricitabine, Lamivudine, Stavudine, Tenofovir alafenamide, Tenofovir disoproxil fumarate, Zidovudine, Delavirdine, Doravirine, Efavirenz, Etravirine, Nevirapine, Rilprivirine, Atazanavir, Darunavir, Fosamprenavir, Indinavir, Lopinavir plus ritonavir, Nelfinavir, Ritonavir, Saquinavir, Tipraniavir, Enfuvirtide, Maraviroc, Bictegravir, Dolutegravir, Elvitegravir, Raltegravir, Atazanavir plus cobicistat, Elvitegravir plus TDF plus FTC plus cobicistat, Abacavir plus lamivudine, Abacavir plus lamivudine plus zidovudine, Atazanavir plus cobicistat, Bictegravir plus tenofovir alafenamide plus emtricitabine, Darunavir plus cobicistat, Darunavir plus cobicistat plus tenofovir alafenamide plus emtricitabine, Dolutegravir plus abacavir plus lamibudine, Dolutegravir plus rilprivirine, Doravirine plus tenofovir disoproxil fumurate, Efavirenz plus tenofovir disoproxil fumarate plus emtricitabine, Elvitegravir plus cobicistat plus tenofovir disoproxil fumarate plus emtricitabine, Elvitegravir plus cobicistat plus tenofovir disoproxil fumarate, Rilprivine plus tenofovir alafenamide plus emtricitabine, Rilpivirine plus tenofovir disoproxil fumarate plus emtricitabine, Tenofovir alafenamide plus emtricitabine, Tenofovir disoproxil fumarate plus emtricitabine, Tenofovir disoproxil fumarate plus lamivudine or Zidovudine plus lamivudine.

In an embodiment, the transdermal delivery formulation comprises a Cannabidiol and an additional active agent for the treatment of Amyotrophic lateral sclerosis, including one or more of the following, riluzole (Rilutek) or edaravone (Radicava).

In an embodiment, the transdermal delivery formulation comprises a Cannabidiol and an additional active agent for the treatment of Parkinson's disease, including one or more of the following, Benztropine mesylate, Entacapone, Dopar, Larodopa, Levodopa and carbidopa, Pramipexole, Rasagiline, Ropinirole HCl, Rotigotine, Safinamide, Tasmar or Trihexphenidyl.

In an embodiment, the transdermal delivery formulation comprises a Cannabidiol and an additional active agent for the treatment of ulcerative colitis, including one or more of the following, anti-inflammatory medication, sulfa drugs, corticosteroids, immunosuppressive agents, antibiotics, 5-aminosalicyclic acid, Balsalazide, mesalamine, olsalazine, sulfasalazine, immunosuppressants, 6-mercaptopurine, azathioprine, cyclosporine, tacrolimus, adalimumab, adalimumab-atto, adalumumab-adbm, Humira, certolizumab, certolizumab pegol, glimumab, infliximab, infliximab-abda, infliximab-dyyb, Remicade, tofacitinib or vedolizumab.

In some particular embodiments it is desirable to adjust the pH of a transdermal delivery formulation and the pH is adjusted to a level of pH 9-11 or 10-11, which can be done by providing appropriate buffers or simply adjusting the pH with base. In other embodiments, it is desirable to adjust the pH of a transdermal delivery formulation to a level of pH 4-6, which can be done by providing appropriate buffers or simply adjusting the pH with an acid.

In some applications a formulation for transdermal delivery may, for example, comprise: Aveeno®, for example in an amount between about 10-95% w/w; between about 20-85% w/w, between about 20-75% w/w, between about 20-50% w/w.

In another aspect, certain embodiments are directed to a sustained release drug delivery platform releases a therapeutic compound or compounds disclosed and made as a formulation described herein over a period of, without limitation, about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration. In other aspects of this embodiment, a sustained release drug delivery platform releases a therapeutic compound or compounds disclosed herein with substantially first order release kinetics over a period of, without limitation, at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration.

The formulation described in this specification may also comprise more than one therapeutic compound as desired for the particular indication being treated, preferably those with complementary activities that do not adversely affect the other proteins. A transdermal delivery formulation to be used for in vivo administration can be sterile. This can be accomplished, for instance, without limitation, by filtration through sterile filtration membranes, prior to, or following, preparation of a transdermal delivery formulation or other methods known in the art, including without limitation, pasteurization.

Packaging and instruments for administration may be determined by a variety of considerations, such as, without limitation, the volume of material to be administered, the conditions for storage, whether skilled healthcare practitioners will administer or patient self-compliance, the dosage regime, the geopolitical environment (e.g., exposure to extreme conditions of temperature for developing nations), and other practical considerations.

In certain embodiments, kits can comprise, without limitation, one or more cream or lotion comprising one or more formulations described herein. In various embodiments, the kit can comprise formulation components for transdermal, topical, or subcutaneous administration, formulated to be administered as an emulsion coated patch. In all of these embodiments and others, the kits can contain one or more lotion, cream, patch, or the like in accordance with any of the foregoing, wherein each patch contains a single unit dose for administration to a subject.

Imaging components can optionally be included, and the packaging also can include written or web-accessible instructions for using a transdermal delivery formulation. A container can include, for example, a vial, bottle, patch, syringe, pre-filled syringe, tube or any of a variety of formats well known in the art for multi-dispenser packaging.

Methods

Methods for treating, preventing or ameliorating a disease, disorder, a condition, or a symptom thereof or a condition related thereto are provided herein using a transdermal delivery formulation for transdermal delivery described herein below. The methods provided herein may comprise or consist of topically administering one or more of a transdermal delivery formulation described herein to skin of a subject in need thereof. Preferred, but non-limiting embodiments are directed to methods for treating, preventing, inhibiting or ameliorating a disease, disorder, a condition, or a symptom described below.

In some embodiments, a suitable transdermal delivery formulation comprises: Siligel™ in an amount less than about 5% w/w; water in an amount between about 10-65% w/w; isopropyl palmitate in an amount between about 0.5-10% w/w; stearic Acid in an amount between about 0.25-10% w/w; cetyl alcohol in an amount between about 0.25-10% w/w; glycerin in an amount between about 0.25-5% w/w; a transdermal delivery formulation in an amount between about 0.25-10% w/w; ethanol in an amount less than about 5% w/w; benzyl alcohol in an amount less than about 5% w/w; sodium hydroxide 50% w/v in an amount between about 0.1-5% w/w; and CBD in an amount between about 1-32% w/w.

In some embodiments, a suitable transdermal delivery formulation comprises: Aveeno® in an amount between about 20-85% w/w; and CBD in an amount between about 15-45% w/w.

The surprising effects achieved by the formulations and methods of the present invention are in part attributable to an improved transdermal delivery formulation that enhances delivery of a CBD salt through the skin. The present transdermal delivery formulations may include a nonionic surfactant. Applicant has found that by employing CBD with particle sizes as disclosed herein, delivered with the penetrants as disclosed herein, and in some embodiments providing a combination of a nonionic surfactant and a polar gelling agent, the penetration capabilities of the CBD of the resulting formulation and the effective level of delivery of the CBD has been enhanced.

In a transdermal delivery formulation, penetrants are based on combinations of an alcohol, such as benzyl alcohol to provide a concentration of 0.5-20% w/w of the final formulation with a transdermal delivery formulation present to provide 25-70% w/w of the formulation. These penetrants are also useful when the agent is a buffer, such as sodium bicarbonate, but less of a transdermal delivery formulation may be required—e.g. less than 12% w/w when the CBD is present at high concentration as disclosed herein.

In some embodiments, the buffering component is any mildly basic compound or combination that will result in a pH of 7-8 in the microenvironment of the tumor cells. In some embodiments, the formulation has a pH of 7-10. Such buffers, in addition to CBD, include lysine buffers, chloroacetate buffers, tris buffers (i.e., buffers employing tris (hydroxymethyl) aminoethane), phosphate buffers and buffers employing non-natural amino acids with similar pKa values to lysine. In some embodiments, the carbonate and/or bicarbonate salt is in an amount between about 7-32% w/w of the formulation. For example, the enantiomers of native forms of such amino acids or analogs of lysine with longer or shorter carbon chains or branched forms thereof. Histidine buffers may also be used. Typically, the concentration of buffer in the compositions is in the range of 10-50% w/w. More typical ranges for sodium bicarbonate or sodium carbonate or both are 10-35% w/w. In some embodiments, the CBD is in an amount between about 15-32% w/w of the formulation.

Alternatively, the penetrant component comprises a completion component as well as one or more electrolytes sufficient to impart viscosity and viscoelasticity, one or more surfactants and an alcohol. The completion component can be a polar liquid, a non-polar liquid or an amphiphilic substance.

The percentage of CBD in a transdermal delivery formulation will depend upon the amount required to be delivered in order to have a useful effect on treating the disorder. In general, the CBD may be present in the formulation in an amount as low as 1% w/w up to about 50% w/w. Typical concentrations may include 15-32% w/w. Since the required percentage of CBD depends on the frequency of administration, as well as the time allotted for administration for each application, the level of CBD may be varied over a wide range. In some embodiments, the CBD is milled to a particle size less than 200 µm. In some embodiments, the CBD is milled to a particle size is less than 70 µm. In some embodiments, the CBD is milled to a particle size less than 70 µm, wherein the CBD is solubilized in the formulation in an amount less than 20% w/w of a transdermal delivery formulation. In some embodiments, the CBD is milled to a particle size less than 70 µm, wherein particle sizes less than about 10 µm have an enhanced penetration thru the skin of a subject. In some embodiments, the CBD is jet milled to a particle size less than about 70 µm. In some embodiments, the CBD has a particle size distribution less than 70 µm.

A transdermal delivery formulation of the disclosure may be prepared in a number of ways. Typically, the components of a transdermal delivery formulation are simply mixed together in the required amounts. However, it is also desirable in some instances to, for example, carry out dissolution of CBD and then add a separate preparation containing the components aiding the delivery of the CBD in the form of a carrier. The concentrations of these components in the carrier, then, will be somewhat higher than the concentrations required in a final transdermal delivery formulation. Thus, CBD may first be dissolved in water and then added to a carrier comprising an alcohol, a transdermal delivery formulation and optionally a combination of a nonionic surfactant and polar gelling agent, or of ionic detergent. Alternatively, some subset of these components can first be mixed and then "topped off" with the remaining components either simultaneously or sequentially. The precise manner of preparing a transdermal delivery formulation will depend on the choice of a CBD and the percentages of the remaining components that are desirable with respect to that CBD. In some embodiments, the water is in an amount between about 10-85% w/w, 15-50% w/w, or 15-45% w/w of the formulation.

The transdermal delivery formulation is a multi-component mixture, whereby the particular concentrations of the penetration enhancers are informed in part by the molecular mass of the CBD and a therapeutic agent. A transdermal delivery formulation enables the CBD and therapeutic agent to become bio-available to the target site within minutes of topical administration. A transdermal delivery formulation permit the use of minimal concentrations of therapeutic agents, as little as. 1/1000th of concentrations required of alternative processes, while enabling bioactivity and positive clinical outcomes simultaneously. In some embodiments, the transdermal delivery formulation comprises an alcohol in an amount less than 5% w/w of the formulation.

Administration and Dosing

A transdermal delivery formulation provided herein can be topically administered in any form. For administration for the treatment of skin conditions a sufficient amount of the topical composition can be applied onto a desired area and surrounding skin, for example, in an amount sufficient to cover a desired skin surface. A transdermal delivery formulation can be applied to any skin surface, including for example, facial skin, and the skin of the hands, neck, chest and/or scalp.

In applying a transdermal delivery formulation of the invention, a transdermal delivery formulation itself is simply placed on the skin and spread across the surface and/or massaged to aid in penetration. The amount of transdermal delivery formulation used is typically sufficient to cover a desired surface area. In some embodiments, a protective cover is placed over the formulation once it is applied and left in place for a suitable amount of time, i.e., 5 minutes, 10 minutes, 20 minutes or more; in some embodiments an hour or two. The protective cover can simply be a bandage including a bandage supplied with a cover that is impermeable to moisture. This essentially locks in the contact of a transdermal delivery formulation to the skin and prevents distortion of a transdermal delivery formulation by evaporation in some cases. The composition may be applied to the skin using standard procedures for application such as a brush, a syringe, a gauze pad, a dropper, or any convenient applicator. More complex application methods, including the use of delivery devices, may also be used, but are not required. In an alternative to administering topically to intact skin, the surface of the skin may also be disrupted mechanically by the use of spring systems, laser powered systems, systems propelled by Lorentz force or by gas or shock waves including ultrasound and may employ microdermabrasion such as by the use of sandpaper or its equivalent or using microneedles or electroporation devices. Simple solutions of the agent(s) as well as the above-listed formulations that penetrate intact skin may be applied using occlusive patches, such as those in the form micro-patches. External reservoirs of the formulations for extended administration may also be employed.

In an alternative to administering topically to intact skin, the surface of the skin may also be disrupted mechanically by the use of spring systems, laser powered systems, use of iontophoresis, systems propelled by Lorentz force or by gas or shock waves including ultrasound and may employ microdermabrasion such as by the use of sandpaper or its equivalent or using microneedles or electroporation devices. Simple solutions of the agent(s) as well as the above-listed transdermal delivery formulations that penetrate intact skin may be applied using occlusive patches, such as those in the form micro-patches. External reservoirs of the formulations for extended administration may also be employed.

Accordingly, in certain embodiments alternative methods of administering one or more buffering agent, CBD with or without another therapeutic agent through intact skin are provided. As nonlimiting examples, these alternative methods might be selected from the following lists: on basis of working mechanism, spring systems, laser powered, energy-propelled, Lorentz force, gas/air propelled, shock wave (including ultrasound), on basis of type of load, liquid, powder, projectile, on basis of drug delivery mechanism, nano-patches, sandpaper (microdermabrasion), iontophoresis enabled, microneedles, on basis of site of delivery, intradermal, intramuscular, and subcutaneous injection. Other suitable delivery mechanisms include, without limitation, microneedle drug delivery, such as 3M Systems, Glide SDI (pushes drug as opposed to "firing" drug), MIT low pressure injectors, micropatches (single use particle insertion device), microelectro mechanical systems (MEMS), dermoelectroporation devices (DEP), transderm ionto system (DEP), TTS transdermal therapeutic systems, membrane-moderated systems (drug reservoir totally encapsulated in a shallow compartment), adhesive diffusion-controlled system (drug reservoir in a compartment fabricated from drug-impermable metallic plastic backing), matrix dispersion type system (drug reservoir formed by homogeneously dispersing drug solids in a hydrophilic or lipophilic polymer matrix molder into medicated disc), and microreservoir system (combination of reservoir and matrix dispersion-type drug delivery system).

The application method is determined by the nature of the treatment but may be less critical than the nature of a transdermal delivery formulation itself. If the application is to a skin area, it may be helpful in some instances to prepare the skin by cleansing or exfoliation. In some instances, it is helpful to adjust the pH of the skin area prior to application of the formulation itself. The application of a transdermal delivery formulation may be by simple massaging onto the skin or by use of devices such as syringes or pumps. Patches could also be used. In some cases, it is helpful to cover the area of application to prevent evaporation or loss of a transdermal delivery formulation.

Where the application area is essentially skin, it is helpful to seal-off the area of application subsequent to supplying a transdermal delivery formulation and allowing the penetration to occur so as to restore the skin barrier. A convenient way to do this is to apply a composition comprising linoleic acid which effectively closes the entrance pathways that were provided by the penetrants of the invention. This application, too, is done by straightforward smearing onto the skin area or can be applied more precisely in measured amounts.

In some embodiments, the disclosure is directed to administering a therapeutic agent in combination with a formulation or method provided herein. A wide variety of therapeutic agents may be used in combination with CBD in a transdermal delivery formulation or compositions and formulations for other routes of administration, including anesthetics, fat removal compounds, nutrients, nonsteroidal anti-inflammatory drugs (NSAIDs) agents for the treatment of migraine, antifungal agents, anti-viral agents, wound healing compounds, compounds useful to effect smoking cessation, agents for prevention or treatment of epilepsy, and generally any therapeutic or prophylactic agent in combination with CBD for which transdermal delivery is desired. As noted above, the delivery may simply affect transport across the skin into a localized subdermal location, such as treatment of nail fungus or modulation of hair growth or may affect systemic delivery such as is desirable in some instances where vaccines are used.

For administration of anesthetics as the therapeutic agent in combination with CBD, the local anesthetic may be one or more of the following: benzocaine, lidocaine, tetracaine, bupivacaine, cocaine, etidocaine, mepivacaine, pramoxine, prilocaine, procaine, chloroprocaine, oxyprocaine, paracaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof. Combinations of anesthetic agents may also be used. The anesthetic agent{s) are included in the composition in effective amount(s). Depending on the anesthetic(s) the amounts of anesthetic or combination is typically in the range of 1% w/w to 50% w/w. The compositions of the invention provide rapid, penetrating relief that is long lasting. The pain to be treated can be either traumatic pain and/or inflammatory pain.

Additional therapeutic agents that can be administered in combination with CBD include, hydrocortisone or hydrocortisone acetate may be included in an amount ranging from 0.25% w/w to about 0.5% w/w. Menthol, phenol, and terpenoids, e.g., camphor, can be incorporated for cooling pain relief. For example, menthol may be included in an amount ranging from about 0.1% w/w to about 1.0% w/w.

A transdermal delivery formulation can be applied in a single, one-time application, once a week, once a bi-week, once a month, or from one to twelve times daily, for a period of time sufficient to alleviate a condition, disease, disorder, symptoms, for example, for a period of time of one week, from 1 to 12 weeks or more, from 1 to 6 weeks, from 2 to 12 weeks, from 2 to 12 weeks, from 2 to 8 weeks, from 2 to 6 weeks, from 2 to 4 weeks, from 4 to 12 weeks, from 4 to 8 weeks, or from 4 to 6 weeks. The present compositions can be administered, for example, at a frequency of once per day to hourly if needed. The presently described formulations can be topically administered once or more per day for a period of time from 1 week to 4 weeks, of from 1 week to 2 weeks, for 1 week, for 2 weeks, for 3 weeks, for 4 weeks, or for 4 weeks or more. In some instances, it may also be desirable to continue treatment indefinitely for example to inhibit or prevent carcinogenesis or for improving, extending the duration of remission, or maintaining remission of a cancer or another disease or disorder. A suitable administration for a transdermal delivery formulation comprising a skin cream, lotion or ointment, for example is once, twice, three, four times daily, or hourly if needed.

As described above, if desired, other therapeutic agents can be employed in conjunction with CBD. The amount of active ingredients that may be combined with the carrier materials to produce a single dosage form will vary depending upon the host treated, the nature of the disease, disorder, or condition, and the nature of the active ingredients.

It is understood that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; the area to be treated and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time can be determined by methods well known in the art.

A transdermal delivery formulation in accordance with the subject matter described herein may be a topical dosage form packaged in, for example, a multi-use or single-use package, including for example, a tube, a bottle, a pump, a container or bottle, a vial, a jar, a packet, or a blister package.

Single dosage kits and packages containing a once per day amount of the transdermal delivery formulation may be prepared. Single dose, unit dose, and once-daily disposable containers of the transdermal delivery formulation are also provided.

The present transdermal delivery formulation remains stable in storage for periods including up to about 5 years, between about 3 months and about 5 years, between about 3 months and about 4 years, between about 3 months and about 3 years, and alternately any time period between about 6 months and about 3 years.

A transdermal delivery formulation described herein remains stable for up to at least 3 years at a temperature of less than or equal to 40° C. In an embodiment, the presently described transdermal delivery formulation remains stable for at least 2 years at a temperature of less than or equal to 40° C. In an embodiment, the presently described transdermal delivery formulation remains stable for at least 3 years at a temperature of less than or equal to 40° C. and at a humidity of up to 75% RH, for at least 2 years at a temperature of less than or equal to 40° C. and at a humidity of up to 75% RH, or for at least 3 years at a temperature of less than or equal to 30° C. and at a humidity of up to 75% RH. In a further embodiment, the presently described transdermal delivery formulation in accordance with the subject matter described herein remains stable for an extended period of time when packaged in a multi-use container such as a bottle dispenser or the like, and exhibits equal to or even greater stability when packaged in a single-use package.

In another aspect, the transdermal delivery formulation of certain embodiments comprises a daily dose of particular buffering compound (e.g. sodium bicarbonate, sodium carbonate, magnesium carbonate, potassium carbonate, potassium bicarbonate, TRIS, Lysine, IEPA, etc.). A daily dose for topical or transdermal administration of a transdermal delivery formulation depends on the compound and animal and may be easily determined by the skilled artisan, a suitable amount is about 1 mg/kg to about 5 g/kg, and more typically the daily dose is about 10 mg/kg to about 5 g/kg, about 25 mg/kg to about 2000 mg/kg, about 50 mg/kg to about 2000 mg/kg, about 25 mg/kg to about 1000 mg/kg, about 50 mg/kg to about 1000 mg/kg, about 100 mg/kg to about 700 mg/kg, about 100 mg/kg to about 500 mg/kg, about 150 mg/kg to about 500 mg/kg, about 150 mg/kg to about 400 mg/kg, about 200 mg/kg to about 500 mg/kg, about 200 mg/kg to about 450 mg/kg, about 200 mg/kg to about 400 mg/kg, about 250 mg/kg to about 450 mg/kg, about 250 mg/kg to about 400 mg/kg, about 250 mg/kg to about 350 mg/kg, and about 275 mg/kg to about 325 mg/kg.

If desired, other therapeutic agents can be employed in conjunction with CBD. The amount of active ingredients that may be combined with the carrier materials to produce a single dosage form will vary depending upon the host treated, the nature of the disease, disorder, or condition, and the nature of the active ingredients.

It is understood that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; the area to be treated and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time can be determined by methods well known in the art.

A transdermal delivery formulation in accordance with the subject matter described herein may be a topical dosage form packaged in, for example, a multi-use or single-use package, including for example, a tube, a bottle, a pump, a container or bottle, a vial, a jar, a packet, or a blister package.

Single dosage kits and packages containing a once per day amount of the transdermal delivery formulation may be prepared. Single dose, unit dose, and once-daily disposable containers of the transdermal delivery formulation are also provided.

The present transdermal delivery formulation remains stable in storage for periods including up to about 5 years, between about 3 months and about 5 years, between about 3 months and about 4 years, between about 3 months and about 3 years, and alternately any time period between about 6 months and about 3 years.

Alternatively, a suitable dose for topical or transdermal administration of a CBD is at least about 100 mg, at least about 500 mg, at least about 1 g, at least about 5 g, at least about 10 g, at least about 15 g, at least about 16 g, at least about 17 g, at least about 18 g, at least about 19 g, at least about 20 g, at least about 21 g, at least about 22 g, at least about 23 g, at least about 24 g, at least about 25 g, at least about 26 g, at least about 27 g, at least about 28 g, at least about 29 g, at least about 30 g, at least about 35 g, at least about 40 g, at least about 45 g, at least about 50 g, at least about 60 g, at least about 75 g, at least about 100 g, at least about 200 g, at least about 500 g, or at least about 1.0 kg. This does may be administered daily, twice a day, three times a day, four times a day, five times a day, or more than five times a day.

Aspects of the present specification disclose that the symptoms associated with a disease or disorder described herein are reduced following application of a transdermal delivery formulation with CBD with or without a therapeutic agent by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% and the severity associated with a disease or disorder described herein is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. Aspects of the present specification disclose the symptoms associated with disease or disorder are reduced following application of a transdermal delivery formulation with CBD with or without a therapeutic agent by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect, in certain embodiments a CBD is administered topically or transdermally such that the dose results in a subject intake of at least about 0.1 nmol/hr/Kg, at least about 0.5 nmol/hr/Kg, at least about 0.7 nmol/hr/Kg, at least about 1.0 nmol/hr/Kg, at least about 1.1 nmol/hr/Kg, at least about 1.2 nmol/hr/Kg, at least about 1.3 nmol/hr/Kg, at least about 1.4 nmol/hr/Kg, at least about 1.5 nmol/hr/Kg, at least about 1.6 nmol/hr/Kg, at least about 1.7 nmol/hr/Kg, at least about 1.8 nmol/hr/Kg, at least about 1.9 nmol/hr/Kg, at least about 2.0 nmol/hr/Kg, at least about 2.5 nmol/hr/Kg, at least about 3.0 nmol/hr/Kg, at least about 3.5 nmol/hr/Kg, at least about 4.0 nmol/hr/Kg, at least about 5 nmol/hr/Kg, at least about 10 nmol/hr/Kg, at least about 25 nmol/hr/Kg, at least about 50 nmol/hr/Kg, at least about 100 nmol/hr/Kg, at least about 500 nmol/hr/Kg, or at least about 1 µmol/hr/Kg, In another aspect, in certain embodiments a CBD is administered topically or transdermally such that the dose results in a peak plasma concentration of a buffering or pH modulating compound ranges from about 1 µg/ml to 50 µg/ml, about 5 µg/ml to about 45 µg/ml, about 5 µg/ml to about 40 µg/ml, about 5 µg/ml to about 35 µg/ml, about 5 µg/ml to about 30 µg/ml, about 5 µg/ml to about 25 µg/ml, about 1 µg/ml to about 45 µg/ml, about 1 µg/ml to about 40 µg/ml, about 1 µg/ml to about 35 µg/ml, about 1 µg/ml to about 30 µg/ml, about 1 µg/ml to about 25 µg/ml, about 1 µg/ml to about 20 µg/ml, about 1 µg/ml to about 15 µg/ml, about 1 µg/ml to about 10 µg/ml, about 1 µg/ml to about 9

µg/ml, about 1 µg/ml to about 8 µg/ml, about 1 µg/ml to about 7 µg/ml, about 1 µg/ml to about 6 µg/ml, and about 1 µg/ml to about 5 µg/ml.

In another aspect, in certain embodiments a CBD is administered topically or transdermally so that plasma concentration ranges from about 1 ng/ml to 500 µg/ml, about 10 ng/ml to 500 µg/ml, about 100 ng/ml to 500 µg/ml, about 1 µg/ml to 500 µg/ml, about 10 µg/ml to 500 µg/ml, about 25 µg/ml to 500 µg/ml, about 25 µg/ml to about 450 µg/ml, about 25 µg/ml to about 400 µg/ml, about 25 µg/ml to about 350 µg/ml, about 25 µg/ml to about 300 µg/ml, about 25 µg/ml to about 250 µg/ml, about 50 µg/ml to about 500 µg/ml, about 55 µg/ml to about 500 µg/ml, about 60 µg/ml to about 500 µg/ml, about 65 µg/ml to about 500 µg/ml, about 70 µg/ml to about 500 µg/ml, about 75 µg/ml to about 500 µg/ml, about 80 µg/ml to about 500 µg/ml, about 85 µg/ml to about 500 µg/ml, about 90 µg/ml to about 500 µg/ml, about 95 µg/ml to about 500 µg/ml, about 100 µg/ml to about 500 µg/ml, about 110 µg/ml to about 500 µg/ml, about 120 µg/ml to about 500 µg/ml, about 130 µg/ml to about 500 µg/ml, about 140 µg/ml to about 500 µg/ml about 150 µg/ml to about 500 µg/ml, about 160 µg/ml to about 500 µg/ml, about 170 µg/ml to about 500 µg/ml, about 180 µg/ml to about 500 µg/ml, about 200 µg/ml to about 500 µg/ml, about 200 µg/ml to about 490 µg/ml, about 200 µg/ml to about 480 µg/ml, about 200 µg/ml to about 470 µg/ml, about 200 µg/ml to about 460 µg/ml, about 200 µg/ml to about 450 µg/ml, about 200 µg/ml to about 440 µg/ml, about 200 µg/ml to about 430 µg/ml, or about 200 µg/ml to about 400 µg/ml.

In further embodiments, a CBD is administered topically or transdermally so that plasma concentration is at least 10 ng/ml, at least 25 ng/ml, at least 50 ng/ml, at least 100 ng/ml, at least 250 ng/ml, at least 0.5 µg/ml, at least 0.75 µg/ml, at least 1 µg/ml, at least 2 µg/ml, at least 3 µg/ml, at least 4 µg/ml, at least 5 µg/ml, at least 6 µg/ml, at least 7 µg/ml, at least 8 µg/ml, at least 9 µg/ml, at least 10 µg/ml, at least 15 µg/ml, at least 20 µg/ml, at least 25 µg/ml, at least 30 µg/ml, at least 35 µg/ml, at least 40 µg/ml, at least 45 µg/ml, at least 50 µg/ml, at least 55 µg/ml, at least 60 µg/ml, at least 65 µg/ml, at least 70 µg/ml, at least 75 µg/ml, at least 80 µg/ml, at least 85 µg/ml, at least 90 µg/ml, at least 95 µg/ml, at least 100 µg/ml or more than 100 µg/ml.

In another aspect, a CBD is administered topically or transdermally so that peak plasma concentration is reached in 10 min, 15 min, 20 min, 30 min, 45 min, 60 min, 75 min, 90 min, 2 hr, 3 hr, 4 hr, 5 hr, 6 hr, 7 hr, 8 hr, 10 hr, 12 hr or 24 hr after administration.

Aspects of the present specification disclose that the symptoms associated with a disease or disorder described herein are reduced following administration of a transdermal delivery formulation with CBD by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% and the severity associated with a disease or disorder described herein is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. Aspects of the present specification disclose the symptoms associated with disease or disorder are reduced by CBD by about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A transdermal delivery formulation as described herein can be used in the manufacture of medicaments and for the treatment of humans and other animals by administration in accordance with conventional procedures.

Dosing can be single dosage or cumulative (serial dosing), and can be readily determined by one skilled in the art. A transdermal delivery formulation of the present invention may be administered once, twice, three, four, five, six, seven, eight, nine, ten, eleven, twelve, thirteen, fourteen, fifteen, sixteen, seventeen, eighteen, nineteen, twenty or more times to a subject. For instance, treatment of a disease may comprise a one-time administration of an effective dose of a transdermal delivery formulation with CBD as disclosed herein. Alternatively, treatment of a disase may comprise multiple administrations of an effective dose of a transdermal delivery formulation with CBD as carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a transdermal delivery formulation with CBD as disclosed herein can be administered to an individual once daily for an indefinite period of time, or until the individual no longer requires therapy. A person of ordinary skill in the art will recognize that the condition of the individual can be monitored throughout the course of treatment and that the effective amount of a transdermal delivery formulation with CBD disclosed herein that is administered can be adjusted accordingly. In one embodiment, a transdermal delivery formulation as disclosed herein is capable of decreasing the time to resolve the symptoms of a disease through the application of CBD, including in an individual suffering from a disease by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment.

Wde variations in the necessary effective amount are to be expected in view of the differing efficiencies of the various routes of administration. For instance, oral administration of an anti-cancer transdermal delivery formulation disclosed herein generally would be expected to require higher dosage levels than administration by inhalation. Similarly, systemic administration of an anti-cancer transdermal delivery formulation disclosed herein would be expected to require higher dosage levels than a local administration. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors. One skilled in the art will recognize that the condition of the individual can be monitored throughout the course of therapy and that the effective amount of a cancer therapeutic disclosed herein that is administered can be adjusted accordingly.

Aspects of the present specification disclose, in part, reduction or maintenance of cancer cell population and/or tumor cell size in an individual. As used herein, the term "treating," refers to reduction or maintenance of cancer cell population and/or tumor cell size in an individual. For example, the term "treating" can mean reduction or maintenance of cancer cell population and/or tumor cell size levels in an individual by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with cancer, including the detection of cancer cell population and/or tumor cell size are well known and can be determined by a person of ordinary skill in the art by using commonly known testing means, including blood tests, CT scans sonagrams and other tests known to those of ordinary skill. Those of skill in the art will know the appropriate symptoms or indicators associated with cancer and will know how to determine if an individual is a candidate for treatment as disclosed herein.

A transdermal delivery formulation as disclosed herein is administered to an individual. An individual is typically a human being, but can be an animal, including, but not limited to, dogs, cats, birds, cattle, horses, sheep, goats, reptiles and other animals, whether domesticated or not.

In one aspect, disclosed herein is a formulation for transdermal delivery of CBD with or without a therapeutic agent through the skin, nail or hair follicle of a subject, wherein the formulation comprises a) a transdermal delivery formulation in an amount less than about 60% w/w, comprising i. one or more phosphatides, ii. glucose, and iii. one or more fatty acids; and b) water in an amount less than about 50% w/w.

In some embodiments, the formulation, which herein is a CBD formulation with or without a therapeutic agent comprises a) a transdermal delivery formulation in an amount less than about 60% w/w, comprising i. one or more phosphatides, ii. glucose, and iii. one or more fatty acids; and b) water in an amount less than about 50% w/w, further comprises benzyl alcohol in an amount between about 0.5-5% w/w.

In some embodiments, the transdermal delivery formulation, which herein is a CBD formulation with or without a therapeutic agent comprises benzyl alcohol in an amount less than 5% w/w of the formulation.

In some embodiments, the formulation, which herein is a CBD formulation with or without a therapeutic agent comprises a) a transdermal delivery formulation in an amount less than about 60% w/w, comprising i. one or more phosphatides, ii. glucose, and iii. one or more fatty acids; and b) water in an amount less than about 50% w/w, further comprises Isopropyl Palmitate in an amount between about 5-5% w/w.

In some embodiments, the water is deionized water and/or purified water.

In some embodiments, the water is deionized water and/or purified water.

In some embodiments, the water is in an amount between about 15-40% w/w of the formulation.

In some embodiments, the one or more phosphatides in an amount between about 0.5-55% w/w of the transdermal delivery formulation.

In some embodiments, the transdermal delivery formulation, which herein is a CBD formulation with or without a therapeutic agent comprises phosphatidylcholine, hydrogenated phosphatidylcholine, phosphatidylserine, phosphatidylethanolamine, phosphatidylinositol, or a combination thereof in amount less than 30% w/w of the formulation.

In some embodiments, the one or more phosphatides comprises phosphatidylcholine of the transdermal delivery formulation.

In some embodiments, the one or more fatty acids in an amount between about 1-35% w/w of the transdermal delivery formulation.

In some embodiments, the one or more fatty acids in an amount between about 5-35% w/w of the transdermal delivery formulation.

In some embodiments, the one or more fatty acids comprises Linoleic Acid, Oleic Acid, Stearic Acid, sunflower oil, or a combination thereof.

In some embodiments, the one or more fatty acids comprises Linoleic Acid.

In some embodiments, the one or more fatty acids comprises Oleic Acid.

In some embodiments, the one or more fatty acids comprises Stearic Acid.

In some embodiments, the one or more phosphatides are derived from a seed oil in an amount between about 0.5-55% w/w of the transdermal delivery formulation.

In some embodiments, the one or more phosphatides are derived from a seed oil in an amount between about 5-35% w/w of the transdermal delivery formulation.

In some embodiments, the one or more phosphatides are derived from a safflower oil in an amount between about 0.5-55% w/w of the transdermal delivery formulation.

In some embodiments, the one or more phosphatides are derived from a safflower oil in an amount between about 5-35% w/w of the transdermal delivery formulation.

In some embodiments, the one or more phosphatides are derived from an almond oil in an amount between about 0.5-55% w/w of the transdermal delivery formulation.

In some embodiments, the one or more phosphatides are derived from an almond oil in an amount between about 5-35% w/w of the transdermal delivery formulation.

In some embodiments, the one or more phosphatides comprises one or more fatty acids derived from soy lecithin.

In some embodiments, the glucose in an amount between about 0.05-10% w/w of the transdermal delivery formulation.

In some embodiments, the glucose is anhydrous dextrose in an amount between about 0.05-10% w/w of the transdermal delivery formulation.

In some embodiments, the formulation, which herein is a CBD formulation with or without a therapeutic agent comprises a) a transdermal delivery formulation in an amount less than about 60% w/w, comprising i. one or more phosphatides, ii. glucose, and iii. one or more fatty acids; and b) water in an amount less than about 50% w/w, further comprises a nonionic surfactant in an amount between about 2-25% w/w of the transdermal delivery formulation.

In some embodiments, the formulation, which herein is a CBD formulation with or without a therapeutic agent comprises a) a transdermal delivery formulation in an amount less than about 60% w/w, comprising i. one or more phosphatides, ii. glucose, and iii. one or more fatty acids; and b) water in an amount less than about 50% w/w, further comprises a polar solvent at least in an amount in molar excess of the nonionic surfactant.

In some embodiments, the nonionic surfactant is a poloxamer and the polar solvent is water.

In some embodiments, the formulation, which herein is a CBD formulation with or without a therapeutic agent comprises a) a transdermal delivery formulation in an amount less than about 60% w/w, comprising i. one or more phosphatides, ii. glucose, and iii. one or more fatty acids; and b)

water in an amount less than about 50% w/w, further comprises a polar solvent in an amount less than 5% w/w of the formulation.

In some embodiments, the transdermal delivery formulation, which herein is a CBD formulation with or without a therapeutic agent further comprises a detergent portion in an amount between about 1-30% w/w of the transdermal delivery formulation.

In some embodiments, the detergent portion comprises a nonionic surfactant in an amount between about 2-25% w/w of the transdermal delivery formulation; and a polar solvent in an amount less than 5% w/w of the transdermal delivery formulation.

In some embodiments, the transdermal delivery formulation, which herein is a CBD formulation with or without a therapeutic agent is in an amount between about 10-60% w/w of the transdermal delivery formulation.

In some embodiments, the transdermal delivery formulation comprises an alcohol in an amount less than 10% w/w of the transdermal delivery formulation.

In some embodiments, the transdermal delivery formulation further comprises an alcohol, a surfactant, and a polar solvent.

In some embodiments, the transdermal delivery formulation, which herein is a CBD formulation with or without a therapeutic agent comprises cetyl alcohol in amount less than 5% w/w of the formulation.

In some embodiments, the transdermal delivery formulation, which herein is a CBD formulation with or without a therapeutic agent comprises ethanol in an amount less than 5% w/w of the formulation.

In some embodiments, the transdermal delivery formulation, which herein is a CBD formulation with or without a therapeutic agent comprises glycerine in an amount less than 5% w/w of the formulation.

In some embodiments, the transdermal delivery formulation, which herein is a CBD formulation with or without a therapeutic agent comprises propylene glycol in an amount less than 8% w/w of the formulation.

In some embodiments, the formulation, which herein is a CBD formulation with or without a therapeutic agent comprises a gelling agent in an amount less than 20% w/w of the formulation.

In some embodiments, the formulation, which herein is a CBD formulation with or without a therapeutic agent comprises menthol in an amount between about 0.05-5% w/w of the formulation.

In some embodiments, the formulation, which herein is a CBD formulation with or without a therapeutic agent comprises a) a transdermal delivery formulation in an amount less than about 60% w/w, comprising i. one or more phosphatides, ii. glucose, and iii. one or more fatty acids; and b) water in an amount less than about 50% w/w, further comprises tranexamic acid in an amount less than 5% w/w of the formulation.

In some embodiments, the formulation, which herein is a CBD formulation with or without a therapeutic agent comprises a) a transdermal delivery formulation in an amount less than about 60% w/w, comprising i. one or more phosphatides, ii. glucose, and iii. one or more fatty acids; and b) water in an amount less than about 50% w/w, further comprises a humectant, an emulsifier, an emollient, or a combination thereof.

In some embodiments, the formulation, which herein is a CBD formulation with or without a therapeutic agent, which herein is a CBD formulation with or without a therapeutic agent has a pH of 9-11.

In some embodiments, the formulation, which herein is a CBD formulation with or without a therapeutic agent, which herein is a CBD formulation with or without a therapeutic agent has a pH of 7-10.5.

In some embodiments, the formulation, which herein is a CBD formulation with or without a therapeutic agent comprises a) a transdermal delivery formulation in an amount less than about 60% w/w, comprising i. one or more phosphatides, ii. glucose, and iii. one or more fatty acids; and b) water in an amount less than about 50% w/w, further comprises an active agent.

In some embodiments, the formulation, which herein is a CBD formulation with or without a therapeutic agent comprises a) a transdermal delivery formulation in an amount less than about 60% w/w, comprising i. one or more phosphatides, ii. glucose, and iii. one or more fatty acids; and b) water in an amount less than about 50% w/w, further comprises an active agent component in an amount less than about 60% w/w.

In some embodiments, the cannabinoid is a crystalline cannabidiol.

In another aspect disclosed herein is a method to effect transdermal delivery of a CBD comprising applying to the skin, nails or hair follicles of a subject an effective amount of the formulation comprising a) a transdermal delivery formulation in an amount less than about 60% w/w, comprising i. one or more phosphatides, ii. glucose, and iii. one or more fatty acids; and b) water in an amount less than about 50% w/w, further comprises an active agent.

EXAMPLES

The following non-limiting examples are provided for illustrative purposes only in order to facilitate a more complete understanding of representative embodiments now contemplated. These examples are intended to be a mere subset of all possible contexts in which the components of the formulation may be combined. Thus, these examples should not be construed to limit any of the embodiments described in the present specification, including those pertaining to the type and amounts of components of the formulation and/or methods and uses thereof. Ultimately, the formulations may be utilized in virtually any context where buffering therapy with or without a therapeutic agent(s) is desired.

Example 1

Tumor Responsiveness Testing to Topical Buffering Agents and Proteases

In this experiment, tumor biopsy specimens are incubated in various formulations and mediums, including pH neutral mediums and alkaline mediums to determine responsiveness to buffer therapies in conjunction with Cannabidiol.

Transdermal delivery formulations of the invention are tested in some studies for the ability to modify or reduce protein secretion or in other experiments to inhibit multiple stages of tumor progression with and without coadministration and coformulation of topically applied buffering agents in formulations of the invention.

One measurement in these experiments is to determine if tumor cells are sensitive to particular proteases and by altering their morphology or by acidifying their microenvironment when included in a transdermal formulation that is applied to a patient.

Accordingly, in another aspect a diagnostic test is provided for responsiveness of a patient or subject to one or more protease inhibitor as therapeutic agents. Additional diagnostic test provided herein examine responsiveness to one or more protease inhibitor administered in combination with a formulation comprising one or more buffering agent provided herein or formulated with a formulation comprising one or more buffering agent. Proteases inhibitors are administered alone or in combination with formulations comprising one or more buffering agent provided herein to determine if the tumor cells are pH sensitive and therefore may be more responsive if a buffering agent is included in the therapy.

Example 2—Comparison of Lecithin and Lecithin-Alternative Based Topical Delivery of Cannabidiol (CBD)

In this experiment, transdermal delivery formulation of cannabidiol (CBD) based on formulations of the invention (lecithin-free formulations) were tested for their ability to effect blood serum levels of CBD and compared to similar formulations using transdermal delivery formulations containing lecithin.

In vivo tests were performed as follows: adult CD-1 mice were dosed with one of two topical transdermal delivery formulations of tranexamic acid. Subjects had 83.33 mg/kg of CBD applied one time in a transdermal delivery formulation. Blood was drawn at 15 minutes, 30 minutes, 1 hour, 2 hours, and 4 hours following application of the transdermal delivery formulation with CBD and the blood was tested to determine the CBD concentration in plasma.

Treatment was provided randomly to two groups of patients as follows:
 a. CBD (2.5%) in a transdermal delivery formulation that includes lecithin as set forth below in Table 3; or
 b. CBD (2.5%) in a transdermal delivery formulation based on the lecithin-free formulation set forth below in Table 4.

TABLE 6

CBD Formulation - Lecithin Based Formulation

| Ingredient | wt % |
|---|---|
| Deionized Water | 59.65% |
| Lecithin | 9.03% |
| Isopropyl Palmitate | 7.95% |
| Cetyl Alcohol | 4.82% |
| Benzyl Alcohol | 1.09% |
| Ethanol | 1.13% |
| Caprylic/Capric Triglyceride | 3.27% |
| Propylene Glycol | 2.19% |
| Glycerine | 0.53% |
| Magnesium Chloride | 1.03% |
| D-limonene | 1.03% |
| Crystalline Cannabidiol | 2.50% |
| Durosoft PK-SG | 1.13% |
| Poloxamer (407) | 4.65% |
| Total | 100.00% |

TABLE 7

CBD Formulation - Lecithin-Free Formulation

| Ingredient | Weight % |
|---|---|
| Deionized Water | 59.51% |
| Dextrose Anhydrous | 0.65% |

TABLE 7-continued

CBD Formulation - Lecithin-Free Formulation

| Ingredient | Weight % |
|---|---|
| Phospholipon 90G | 7.47% |
| Isopropyl Palmitate | 13.00% |
| Benzyl Alcohol | 1.36% |
| Stearic Acid | 0.75% |
| Linoleic Acid | 2.53% |
| Oleic Acid | 1.14% |
| D-limonene | 1.00% |
| Crystalline Cannabidiol | 2.50% |
| Durosoft PK-SG | 1.04% |
| Poloxamer (407) | 9.05% |
| Total | 100.00% |

II topical treatments (lecithin based and lecithin free formulations) induced measurable CBD concentration in subject blood plasma. In the lecithin based formulation group, average maximum plasma concentration was 331 ng/mL. In the lecithin free formulation group, average maximum plasma concentration was 427 ng/mL.

Experiment 3 In Vivo Studies with CBD

The objective of this study was to determine the plasma pharmacokinetic (PK) profile of test article cannabidiol (CBD) following the administration of a single topical dose to CD-1 mice. The work was conducted at Alliance Pharma with a title of In-life Study 1901002-01. Although the in-life study was not intended to be conducted in compliance with Good Laboratory Practice regulations, the study was conducted in accordance with Alliance Pharma's IACUC (Institutional Animal Care and Use Committee) Protocol No. 2016-02_V4 and Alliance Pharma's standard operating procedures (SOPs). In addition, the pharmacokinetic analyses of mouse plasma samples were conducted in accordance with Alliance Pharma SOPs.

A total of 72 mouse (CD-1) plasma samples were transferred from Alliance Pharma's in-life facility located in Malvern, Pa. to the Bioanalytical department for pharmacokinetic analysis. The concentration of CBD in these 72 plasma samples was measured using high-performance liquid chromatography (HPLC) with tandem mass spectrometry (MS/MS) detection.

Test Article: The dose gels for test article CBD were provided by Ampersand Biopharma dba Dyve Biosciences (Thousand Oaks, Calif.), prior to the start of this study and stored at room temperature.

Internal Standard, Critical Reagents, and Matrix: The following internal standard, critical reagents, and matrix were used in this study.
 Internal standard tolbutamide was obtained from Sigma-Aldrich Corporation (St. Louis, Mo.) and stored in a refrigerator set at 4° C.
 Acetonitrile (HPLC grade) was obtained from Thermo Fisher Scientific (Waltham, Mass.).
 Blank mouse plasma (with K2 EDTA [tripotassium ethylenediaminetetraacetic acid] as an anticoagulant) was obtained from BioIVT (Westbury, N.Y.). The matrix was stored in a freezer set to −20° C.

In-life Study Design: In-life Study 1901002-01 was performed at the in-life testing facility at Alliance Pharma. Four (4) groups of 21 CD-1 mice each (84 total) were administered a single topical dose of CBD. Mice in Group 1 were administered Formulation A at a strength of 2.5% CBD. Mice in Group 2 were administered Formulation B at the same strength of 2.5% CBD. Mice in Group 3 were administered Formulation C at a strength of 5% CBD, and mice in Group 4 were administered Formulation C at a strength of 2.5% CBD. The treatment scheme is summarized below.

TABLE 8

Treatment Doses of Cannabidiol Administered to CD-1 Mice

| Group | No. of Animals | Formulation | Formulation Strength | Dose (mg/kg) | Mean Dose * (mg/kg) | Dose Volume (pL) |
|---|---|---|---|---|---|---|
| 1 | 21 | AEM.CBD.006 Formulation A | 2.5% CBD | 83.33 | 78.69 | 100 |
| 2 | 21 | AEM.CBD.007 Formulation B | 2.5% CBD | 83.33 | 76.61 | 100 |
| 3 | 21 | KBM.CBD.010 Formulation C | 5% CBD | 166.67 | 155.24 | 100 |
| 4 | 21 | KBM.CBD.011 Formulation C | 2.5% CBD | 83.33 | 75.76 | 100 |

* Mean dose was calculated based on dose gel density and average mouse body weight of 30 grams. The density of formulation AEM.CBD.006 = 0.9443; the density of formulation AEM.CBD.007 = 0.9194; the density of forrindation KBM.CBD.010 = 0.9314; and the density of formuiation KBM.CBD.011 = 0.9091.

Animals in each group received topical administration of either 2.5% o 5% CBD using a 1 ml syringe to draw up exactly 100 μl. Compound was applied in the shaved area only. Each group received a different formulation of the compound.

Visibility checks/mortality checks: Once daily. Clinical Observations: On the day prior to dose administration and on the day of dose administration, at each time point and for 2 weeks post dose. Animals were checked twice daily for normal room checks and no abnormal observations were noted. All animals ate, drank, and groomed accordingly. On the day of dose administration, it was noted that animals in groups 3 and 4 appeared notably more active after application. No other observations were noted.

Sample Collection, Processing, and Shipment: Blood samples were collected at the in-life facility at the following time points: 0.25, 0.5, 1, 2, 4, and 8 hours post-dose from 72 mice in Groups 1 through 4 (18 from each treatment group). Target volume was less than or equal to 0.2 ml. The blood was collected via trunk puncture into tubes using K2 EDTA as an anticoagulant. The collected blood samples were kept on wet ice before being centrifuged. Blood samples were centrifuged as soon as possible after blood collection at approximately 10,000 rpm for about 10 minutes to separate the plasma. Approximately 0.2 mL of each plasma sample was transferred into labeled Eppendorf tubes. Each tube was stored in a freezer set to −20° C. or lower. No blood was collected from 12 (3 from each treatment group) of the 84 mice enrolled in the in-life study; thus, the total number of plasma samples that were transferred to the Alliance Pharma Bioanalytical department for bioanalysis was 72.

Assay Procedures: For analysis of CBD, a 25-μL aliquot of each study sample was mixed with 25 μL of acetonitrile/water (50:50, v/v). Samples were then extracted by protein precipitation using acetonitrile containing the internal standard, tolbutamide (25 ng/mL). A portion of the supernatant was diluted in deionized water and used for the analysis of CBD.

Preparation of Standards and Quality Controls: Calibration standards of CBD mouse plasma samples were prepared in acetonitrile/water (50:50, v/v) at concentrations of 1, 2, 20, 200, 500, 1000, 1800, and 2000 ng/mL. The low quality control (LQC), medium quality control (MQC), and high quality control (HQC) were prepared in blank mouse plasma at concentrations of 3, 150, and 1500 ng/mL, respectively. A dilution quality control (DQC) was prepared at a concentration of 10,000 ng/mL and used in Batch 1.

Sample Analyses: Study samples were analyzed using a bioanalytical method qualified by Alliance Pharma. A total of 1 batch was run. At a minimum, the batch included the following: a calibration curve, a matrix blank (blank mouse plasma), a reagent blank, a control zero (blank mouse plasma spiked with internal standard), and triplicate QC samples at 4 concentration levels (LQC, MQC, HQC, and DQC) in addition to the study samples. Within the batch, the study samples were bracketed by calibration standards or QC samples. The lowest calibration standard served to evaluate system suitability at the beginning of each batch. In all of the batches, the system suitability samples displayed adequate separation and acceptable peak shapes, retention times, and signal-to-noise ratios (>3:1).

A total of 72 mouse plasma samples were transferred from Alliance Pharma's in-life facility to Alliance Pharma's Bioanalytical department. Upon transfer, the samples were stored in a freezer set to −20° C. The concentration of CBD in the 72 mouse plasma samples was measured in 1 analytical batch. Of the 84 mice that had been enrolled in the in-life study, 12 (3 per treatment group) did not have blood samples collected for plasma PK analysis.

Data Acquisition and Processing: The LC-MS/MS data acquisition was performed on a Shimadzu Nexera X2 LC system coupled with an AB SciEx Triple Quad 5500 mass spectrometer. Chromatograms were integrated using Analyst 1.6.2 software. A weighted ($1/x^2$, x=concentration) linear regression was used to generate the calibration curve for CBD. The concentration of CBD was calculated using the peak area ratio of analyte to internal standard based on the standard curve. Mean, standard deviation, precision, accuracy, and assay variability were calculated using Microsoft Excel software.

Data Calculations: The linear formula used to calculate the calibration curves is as follows:

$$y=ax+b$$

where,
y represents the peak area ratio
a represents the slope of the line
x represents the concentration
b represents the y-intercept The standard deviation (SD) was calculated as follows:

$$SD = \sqrt{\frac{\Sigma(x - \bar{x})^2}{n-1}}$$

where,
x represents the sample concentration
x̄ represents the sample mean
n represents the sample size The precision or coefficient of variation (CV), expressed as a percentage, was calculated as follows:

$$\% \ CV = \frac{\text{Standard deviation}}{\text{Mean}} \times 100$$

The accuracy (or the degree of closeness of the measured value to its nominal value), expressed as a percentage, was calculated as follows:

$$\% \ Accuracy = \frac{\text{Measured value}}{\text{Nominal value}} \times 100$$

The deviation or DEV (of the measured value from its nominal), expressed as a percentage, was calculated as follows:

$$\% \ DEV = \frac{\text{Measured value} - \text{Nominal value}}{\text{Nominal value}} \times 100$$

Acceptance Criteria: The analytical batches were accepted if the calibration standards and the QC data met the acceptance criteria described below.

Calibration Standards: For a calibration standard to have been accepted, the back-calculated concentration had to be 100%±20% of its nominal concentration. For a batch to have been accepted, a minimum of 67% of standards had to meet this criterion.

Pharmacokinetic Analysis: Software—The PK parameters were determined using a non-compartmental analysis tool, namely, Phoenix WnNonlin 6.3 software (Pharsight Corporation, St. Louis, Mo.).

"BLOQ" (Below the Lower Limit of Quantification) Rule: Concentration data below the lower limit of quantification (LLOQ=1 ng/mL) in mouse plasma were replaced with "BLOQ" and excluded from graphing and PK parameter estimations.

Terminal Half-life Calculation: Time points were automatically selected by a "best fit" model for the terminal half-life ($t_{1/2}$) estimation as the first option. Manual selection was applied when the "best fit" model could not produce a well-defined terminal phase. When the number of detected time points after $t_{max}$ (time to reach maximum plasma concentration) was less than 3, the terminal half-life and $AUC_{INF}$ (area under the concentration vs. time curve from time 0 to infinity) were not calculated.

Results

In-life Observations: No abnormal observations were noted during the in-life phase of the study.

Assay Performance: The results from analysis of the calibration standards and QC samples demonstrated that the method performance was acceptable for this study. The calibration standard results for CBD in mouse plasma are listed in Table 8. The QC sample results for CBD are presented in Table 9. A summary of the concentrations of CBD measured in mouse plasma samples is presented in Table 10 through Table 13, Table for Groups 1 through 4, respectively. The mean dose listed in these 4 tables was calculated based on dose gel density and on an average mouse body weight of 30 grams. Representative chromatograms of the matrix blank (blank rat plasma), control zero (blank mouse plasma spiked with internal standard), LLOQ samples, and upper limit of quantification (ULOQ) samples are presented in Table 8

TABLE 8

Calibration Standard Data for Cannabidiol in Mouse Plasma

| Batch ID | Concentration (ng/mL) | | | | | | | |
|---|---|---|---|---|---|---|---|---|
| | 1 | 2 | 20 | 200 | 500 | 1000 | 1800 | 2000 |
| 1 | 0.985 | 2.070 | 18.857 | 224.815 | 581.066 | 892.908 | 1721.133 | 1804.466 |
| n | 1 | 1 | 1 | 1 | 1 | 1 | 1 | 1 |
| Accuracy (%) | 98.5 | 103.5 | 94.3 | 112.4 | 116.2 | 89.3 | 95.6 | 90.2 |

TABLE 9

Quality Control Data for Cannabidiol in Mouse Plasma

| Batch ID | Concentration (ng/mL) | | | | | | | |
|---|---|---|---|---|---|---|---|---|
| | LQC 3 | DEV (%) | MQC 150 | DEV (%) | HQC 1500 | DEV (%) | DQC 10000 | DEV (%) |
| 1 | 2.881 | −4.0 | 138.700 | −7.5 | 1741.379 | 16.1 | 10430.642 | 4.3 |
| | 2.761 | −8.0 | 130.651 | −12.9 | 1324.379 | −11.7 | 9179.010 | −8.2 |
| | 3.024 | 0.8 | 147.126 | −1.9 | 1503.395 | 0.2 | 8731.344 | −12.7 |
| n | 3 | | 3 | | 3 | | 3 | |
| Mean | 2.889 | | 138.826 | | 1523.051 | | 9446.999 | |
| Accuracy (%) | 96.3 | | 92.6 | | 101.5 | | 94.5 | |

Abbreviations: DQC = Dilution quality control; HQC = High quality control; LQC = Low quality control; MQC = Medium quality control

TABLE 10

Concentrations of Cannabidiol Measured in Group 1 Mouse Plasma Samples

| Animal Number | Group | Formulation | Dose Route Dose Volume Mean Dose * | Time Point (hour) | Concentration (ng/mL) |
|---|---|---|---|---|---|
| 1 | 1 | AEM.CBD.006 | Topical | 0.25 | 2.644 |
| 2 | | Formulation A | 0.1 mL | | 17.093 |
| 3 | | 2.5% CBD | 78.69 mg/kg | | 16.761 |
| 4 | | | | 0.5 | 325.111 |
| 5 | | | | | 365.990 |
| 6 | | | | | 344.709 |
| 7 | | | | 1 | 375.317 |
| 8 | | | | | 526.006 |
| 9 | | | | | 178.472 |
| 10 | | | | 2 | 364.087 |
| 11 | | | | | 621.518 |
| 12 | | | | | 295.841 |
| 13 | | | | 4 | 180.309 |
| 14 | | | | | 383.312 |
| 15 | | | | | 67.807 |
| 16 | | | | 8 | 46.415 |
| 17 | | | | | 23.429 |
| 18 | | | | | 55.563 |

Abbreviation CBD: Cannabidiol
* Mean dose was calculated based on dose gel density and average mouse body weight of 30 grams.

TABLE 11

Concentrations of Cannabidiol Measured in Group 2 Mouse Plasma Samples

| Animal Number | Group | Formulation | Dose Route Dose Volume Mean Dose * | Time Point (hour) | Concentration (ng/mL) |
|---|---|---|---|---|---|
| 22 | 2 | AEM.CBD.007 | Topical | 0.25 | 3.976 |
| 23 | | Formulation B | 0.1 mL | | 36.116 |
| 24 | | 2.5% CBD | 76.61 mg/kg | | 37.156 |
| 25 | | | | 0.5 | 43.780 |
| 26 | | | | | 14.987 |
| 27 | | | | | 107.275 |
| 28 | | | | 1 | 167.141 |
| 29 | | | | | 232.400 |
| 30 | | | | | 84.049 |
| 31 | | | | 2 | 744.233 |
| 32 | | | | | 95.491 |
| 33 | | | | | 241.328 |
| 34 | | | | 4 | 234.903 |
| 35 | | | | | 123.383 |
| 36 | | | | | 446.677 |
| 37 | | | | 8 | 22.912 |
| 38 | | | | | 40.660 |
| 39 | | | | | 39.872 |

Abbreviation: CBD: Cannabidiol
* Mean dose was calculated based on dose gel density and average mouse body weight of 30 grams.

TABLE 12

Concentrations of Cannabidiol Measured in Group 3 Mouse Plasma Samples

| Animal Number | Group | Formulation | Dose Route Dose Volume Mean Dose [a] | Time Point (hour) | Concentration (ng/mL) |
|---|---|---|---|---|---|
| 43 | 3 | KBM.CBD.010 | Topical | 0.25 | 13.334 [b] |
| 44 | | Formulation C | 0.1 mL | | 384.339 |
| 45 | | 5% CBD | 155.24 mg/kg | | 263.302 |
| 46 | | | | 0.5 | 248.447 |
| 47 | | | | | 15.634 [b] |
| 48 | | | | | 53.403 |
| 49 | | | | 1 | 254.502 |
| 50 | | | | | 267.346 |
| 51 | | | | | 338.815 |
| 52 | | | | 2 | 486.125 |
| 53 | | | | | 397.969 |
| 54 | | | | | 303.164 |
| 55 [b] | | | | 4 | 2074.715 [b] |
| 56 | | | | | 667.038 |
| 57 | | | | | 537.297 |
| 58 | | | | 8 | 240.020 |
| 59 | | | | | 123.830 |
| 60 | | | | | 106.688 |

Abbreviation: CBD: Cannabidiol
[a] Mean dose was calculated based on dose gel density and average mouse body weight of 30 grams.
[b] Sample was prediluted to bring the concentration within the measurable range.

TABLE 13

Concentrations of Cannabidiol Measured in Group 4 Mouse Plasma Samples

| Animal Number | Group | Formulation | Dose Route Dose Volume Mean Dose * | Time Point (hour) | Concentration (ng/mL) |
|---|---|---|---|---|---|
| 64 | 4 | KBM.CBD.011 | Topical | 0.25 | 75.654 |
| 65 | | Formulation C | 0.1 mL | | 84.067 |
| 66 | | 2.5% CBD | 75.76 mg/kg | | 78.979 |
| 67 | | | | 0.5 | 114.619 |
| 68 | | | | | 183.153 |
| 69 | | | | | 201.074 |
| 70 | | | | 1 | 413.420 |
| 71 | | | | | 300.142 |
| 72 | | | | | 281.118 |
| 73 | | | | 2 | 237.196 |
| 74 | | | | | 538.811 |
| 75 | | | | | 180.831 |
| 76 | | | | 4 | 132.148 |
| 77 | | | | | 260.930 |
| 78 | | | | | 132.797 |
| 79 | | | | 8 | 45.229 |
| 80 | | | | | 42.760 |
| 81 | | | | | 24.446 |

Abbreviation: CBD: Cannabidiol
* Mean dose was calculated based on dose gel density and average mouse body weight of 30 grams.

Figure 5:
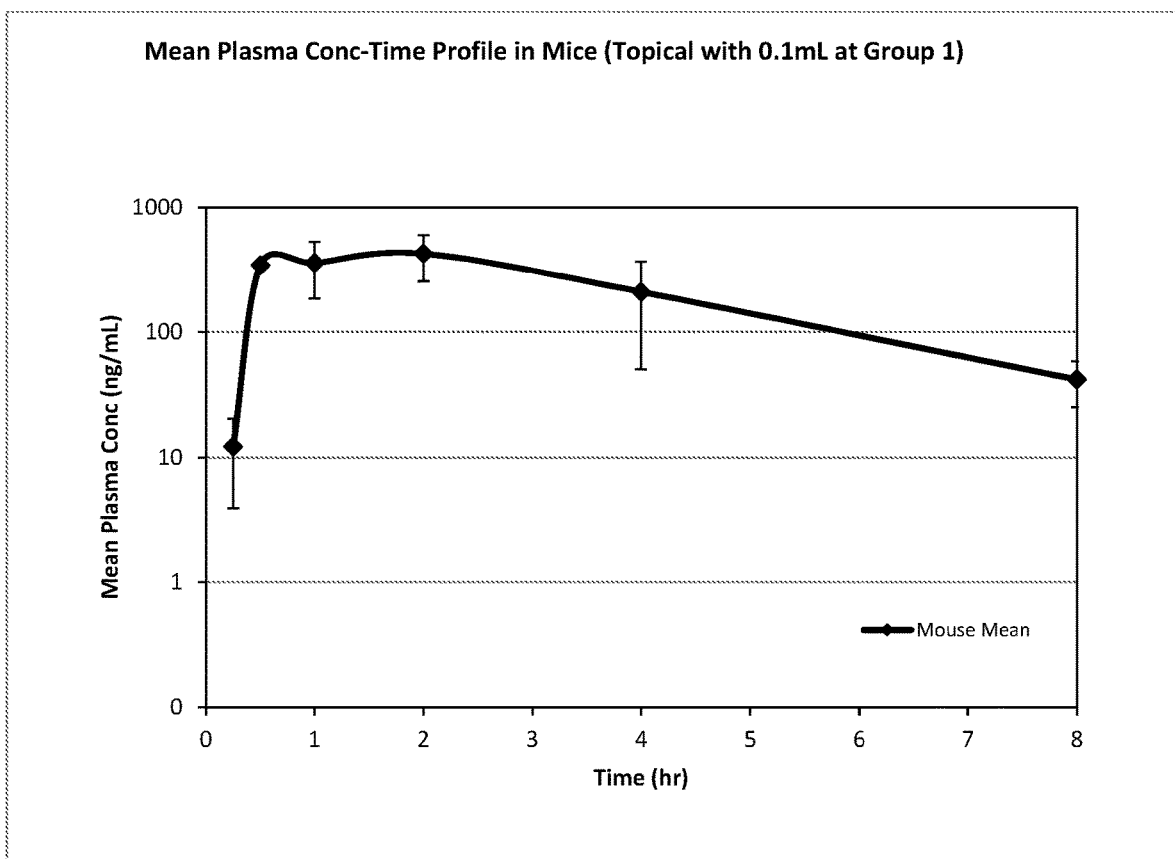
FIG. 5. Mean Plasma Concentration vs. Time Profile in Group 1 Mice After a Single Topical Dose of Cannabidiol at 78.69 mg/kg.
Figure 6:
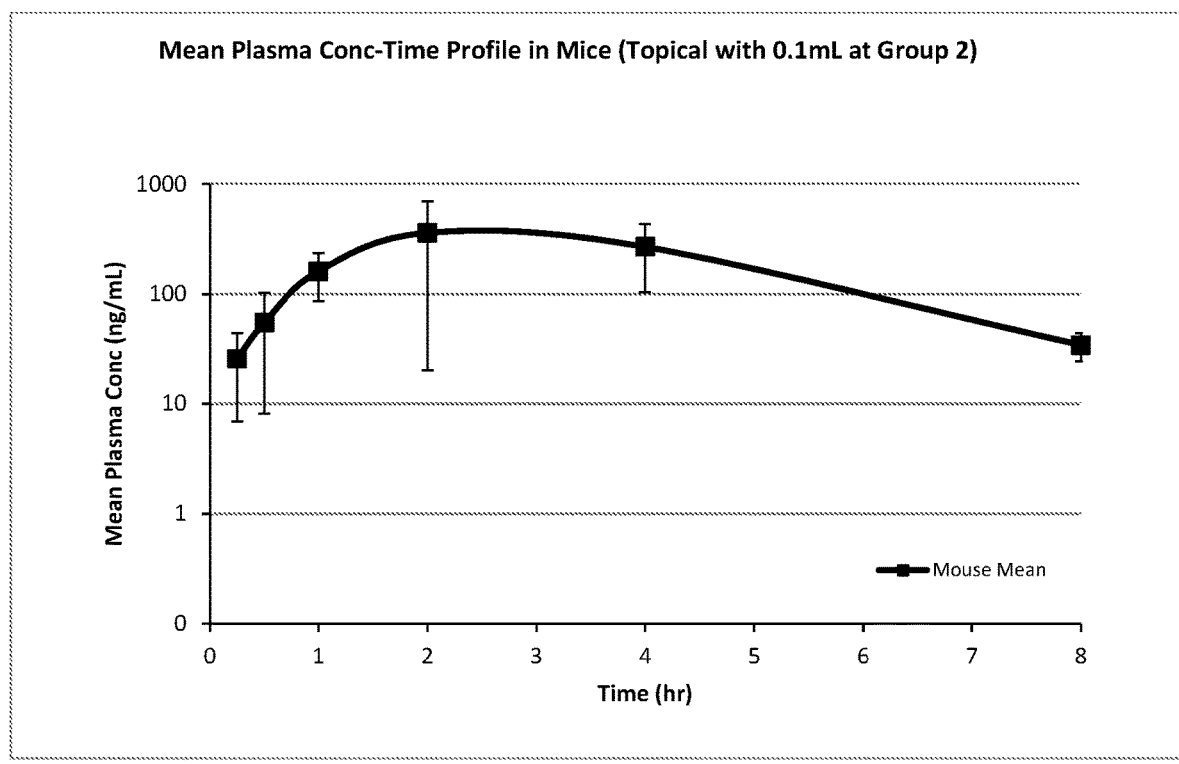
FIG. 6. Mean Plasma Concentration vs. Time Profile in Group 2 Mice After a Single Topical Dose of Cannabidiol at 76.61 mg/kg.
Figure 7:
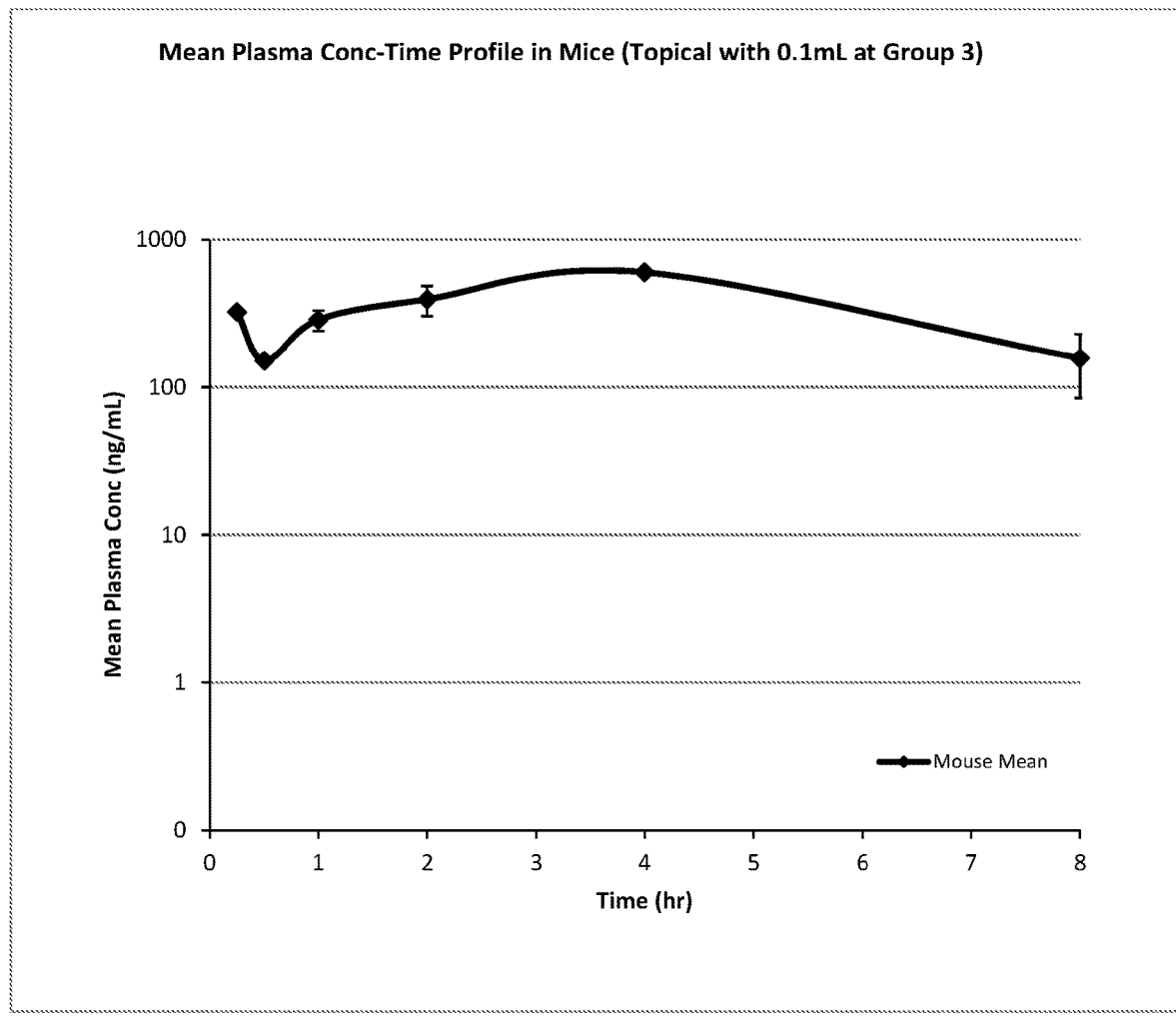
FIG. 7. Mean Plasma Concentration vs. Time Profile in Group 3 Mice After a Single Topical Dose of Cannabidiol at 155.24 mg/kg.
Figure 8:
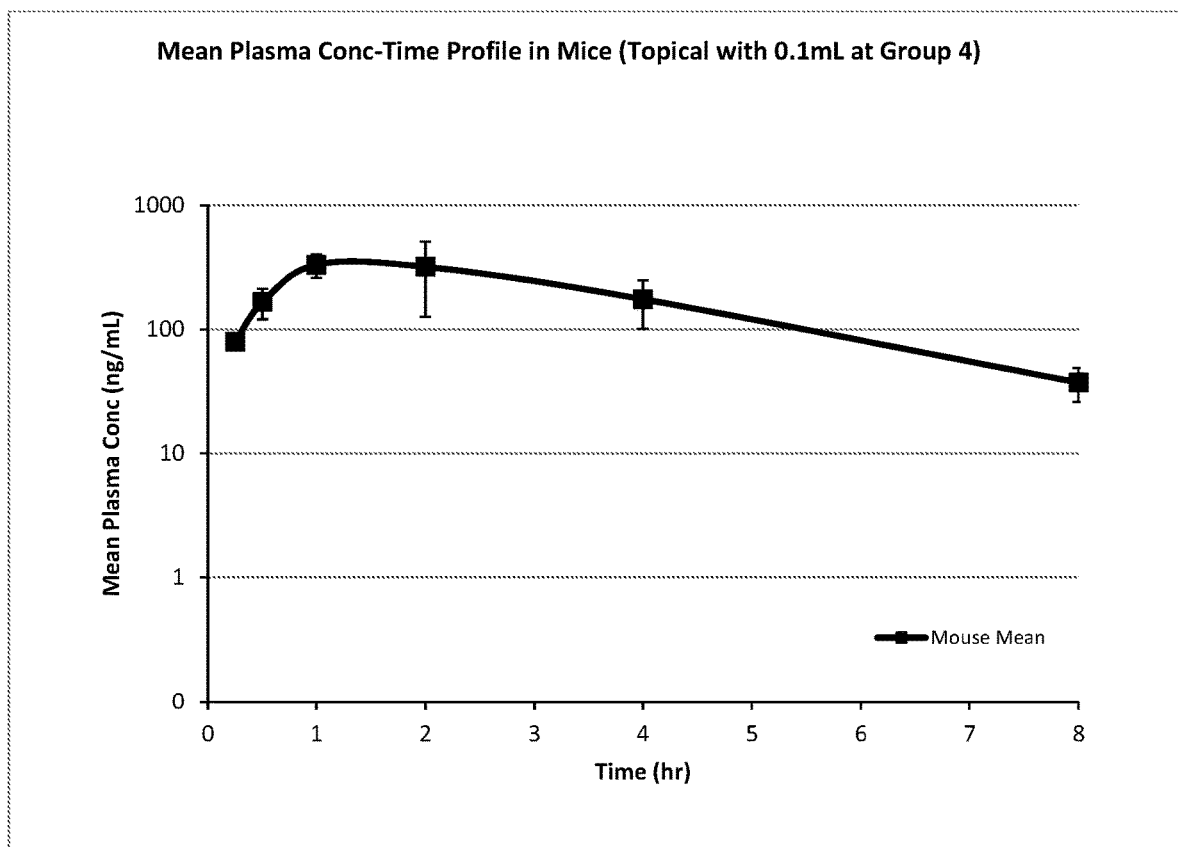
FIG. 8. Mean Plasma Concentration vs. Time Profile in Group 4 Mice After a Single Topical Dose of Cannabidiol at 75.76 mg/kg.

Pharmacokinetic Results: For PK parameter calculations of Group 1, the mean body weight of mice at the time of dosing was used, namely, 30 grams. Thus, the mean dose for Group 1 is 78.69 mg/kg. After a topical dose of 0.1 mL of CBD per mouse, the mean $C_{max}$ in mouse plasma was 427.149 ng/mL, and the corresponding mean $t_{max}$ was 2.00 hours. The mean $AUC_{iast}$ and mean $AUC_{inf}$ were 1758 and 1865 hr·ng/mL, respectively. For PK parameter calculations of Group 2, the mean body weight of mice at the time of dosing was used, namely, 30 grams. Thus, the mean dose for Group 2 is 76.61 mg/kg. After a topical dose of 0.1 mL of CBD per mouse, the mean $C_{max}$ in mouse plasma was 360.351 ng/mL, and the corresponding mean $t_{max}$ was 2.00 hours. The mean $AUC_{last}$ and $AUC_{inf}$ were 1563 and 1647 hr·ng/mL, respectively. For PK parameter calculations of Group 3, the mean body weight of mice at the time of dosing was used, namely, 30 grams. Thus, the mean dose for Group 3 is 155.24 mg/kg. After a topical injection of 0.1 mL of CBD per mouse, the mean $C_{max}$ in mouse plasma was 602.168 ng/mL, and the corresponding mean $t_{max}$ was 4.00 hours. The mean $AUC_{last}$ and $AUC_{inf}$ were 3067 and 3533 hr·ng/mL, respectively. For PK parameter calculations of Group 4, the mean body weight of mice at the time of dosing was used, namely, 30 grams. Thus, the mean dose for Group 4 is 75.76 mg/kg. After a topical injection of 0.1 mL of CBD per mouse, the mean $C_{max}$ in mouse plasma was 331.560 ng/mL, and the corresponding mean $t_{max}$ was 1.00 hours. The mean AUCiast and $AUC_{inf}$ were 1410 and 1514 hr·ng/mL, respectively. The pharmacokinetic parameters of CBD and concentration vs. time data in mouse plasma after topical administration are summarized in Table 14 and illustrated in FIGS. 5 through 8.

TABLE 14

Pharmacokinetic Parameters for a Single Topical Dose of Cannabidiol per Mouse Group

| PK Parameter | Units | Group 1 | Group 2 | Group 3 | Group 4 |
|---|---|---|---|---|---|
| Mean dose | mg/kg | 78.69 | 76.61 | 155.24 | 75.76 |
| $t_{1/2}$ | hr | 1.78 | 1.70 | N/A | 1.92 |
| $t_{max}$ | hr | 2.00 | 2.00 | 4.00 | 1.00 |
| $C_{max}$ | ng/mL | 427.149 | 360.351 | 602.168 | 331.560 |
| Regression points | hr | 2, 4, 8 | 2, 4, 8 | N/A | 2, 4, 8 |
| $AUC_{last}$ | hr·ng/mL | 1758 | 1563 | 3067 | 1410 |
| $AUC_{inf}$ | hr·ng/mL | 1865 | 1647 | 3533 | 1514 |

Example 4 Treatment of a Patient Suffering from Severe Pain

A male patient, age 43 presents with severe pain in his back that requires the patient to take oxycontin on a regular basis. The patient's doctor determines that the patient is at risk of becoming addicted to oxycontin and prescribes a transdermal delivery formulation containing CBD at a concentration of 75 mg/kg applied daily to the back of the patient. Within a few days following application of the transdermal delivery formulation containing CBD, the patient begins to suffer from a reduction of the pain in his back. Over the next few weeks, the amount of pain the patient suffers was reduced by over 50%. The patient continues to apply the transdermal formulation containing CBD to his back with the result that the patient is able to maintain his pain with Tylenol and/or ibuprofen.

A female patient age 16 presents with random seizures that incapacitate the patient. The patient's doctor prescribes a transdermal formulation containing CBD. The patient begins using a transdermal formulation containing CBD at 50 mg/kg, and then two weeks later begins to use a transdermal formulation containing CBD at 75 mg/kg and finally four weeks after starting treatment, the patient is administered CBD at a concentration of 100 mg/kg. Starting around six weeks, the frequency of the seizures suffered by the patient begins to reduce and continues to stay reduced as compared to the period of time before the patient began applying the transdermal formulation with CBD.

A male patient 56 years of age presents with Parkinson's disease. The patient has begun to lose motor function and mental cognition. The doctor prescribes a transdermal formulation with CBD, starting at 20 mg/kg and increasing every two weeks until reaching 75 mg/kg. Within a short period of time following administration of the transdermal formulation with CBD, the severity of the symptoms of Parkinson's disease begin to ameliorate and the onset of new symptoms is slowed.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A transdermal delivery formulation comprising the following components:
   a. Cannabidiol (CBD) at a concentration from 1% to 7%;
   b. a phosphatidylcholine at a concentration from 4% to 15%;
   c. glucose at a concentration from 0% to 3%;
   d. benzyl alcohol at a concentration from 0.25% to 5%;
   e. deionized water at a concentration from 10% to 75%;
   f. safflower oil at a concentration from 1% to 20%;
   g. oleic acid at a concentration from 0.2% to 7.5%;
   h. stearic acid at a concentration from 0.1% to 7%; and
   i. isopropyl palmitate at a concentration from 5% to 30%,
   wherein all amounts are percent by weight relative to the total weight of said transdermal delivery formulation (w/w).

2. The transdermal delivery formulation of claim 1, wherein the transdermal formulation further comprises one or more of a moisturizer, cream, oil or lotion.

3. The transdermal delivery formulation of claim 1, wherein the transdermal formulation further comprises a surfactant.

4. The transdermal delivery formulation of claim 1, wherein the transdermal formulation further comprises a nonionic detergent.

5. The transdermal delivery formulation of claim 1, wherein the transdermal formulation further comprises a polar gelling agent.

6. The transdermal delivery formulation of claim 1, wherein the Cannabidiol (CBD) concentration is from 1.5% to 6%.

7. The transdermal delivery formulation of claim 1, wherein the phosphatidylcholine concentration is from 5% to 10%.

8. The transdermal delivery formulation of claim 1, wherein the glucose is from 0.5% to 2%.

9. The transdermal delivery formulation of claim 1, wherein the benzyl alcohol is from 0.5% to 4%.

10. The transdermal delivery formulation of claim 1, wherein the deionized water is from 10% to 50%.

11. The transdermal delivery formulation of claim 1, wherein the safflower oil is at a concentration from 1% to 20%.

12. The transdermal delivery formulation of claim 1, wherein the safflower oil comprises a linoleic acid.

13. The transdermal delivery formulation of claim 1, wherein the safflower oil is at a concentration from 5% to 19%.

14. The transdermal delivery formulation of claim 1, wherein the oleic acid is at a concentration from 4% to 7%.

15. The transdermal delivery formulation of claim 1, wherein the stearic acid is at a concentration from 0.2% to 5%.

16. The transdermal delivery formulation of claim 1, wherein the isopropyl palmitate is at a concentration from 7% to 20%.

* * * * *